(12) United States Patent
Kleemann

(10) Patent No.: US 7,622,611 B2
(45) Date of Patent: *Nov. 24, 2009

(54) PENTAFLUOROSULFANYLBENZOYL GUANIDINES, PROCESS FOR THEIR PREPARATION, USE AS A MEDICAMENT OR DIAGNOSTIC AID, AND MEDICAMENT COMPRISING SAME

(75) Inventor: Heinz-Werner Kleemann, Frankurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

This patent is subject to a terminal disclaimer.

(21) Appl. No.: 11/972,954

(22) Filed: Jan. 11, 2008

(65) Prior Publication Data

US 2008/0146673 A1 Jun. 19, 2008

Related U.S. Application Data

(63) Continuation of application No. 10/989,069, filed on Nov. 15, 2004, now abandoned.

(60) Provisional application No. 60/555,492, filed on Mar. 23, 2004.

(30) Foreign Application Priority Data

Nov. 13, 2003 (DE) .................. 103 53 202

(51) Int. Cl.
C07C 233/65 (2006.01)
C07C 255/50 (2006.01)
A61K 31/165 (2006.01)

(52) U.S. Cl. .................... 564/162; 514/618
(58) Field of Classification Search .......... 564/162; 514/618
See application file for complete search history.

(56) References Cited

U.S. PATENT DOCUMENTS

| | | | |
|---|---|---|---|
| 5,571,842 A | 11/1996 | Kleemann | |
| 5,591,754 A | 1/1997 | Lang | |
| 5,741,935 A | 4/1998 | Bowden et al. | |
| 5,747,539 A | 5/1998 | Dorsch et al. | |
| 5,851,952 A | 12/1998 | Karp et al. | |
| 5,869,426 A | 2/1999 | Karp et al. | |
| 5,965,491 A | 10/1999 | Wu et al. | |
| 6,080,861 A | 6/2000 | Karp et al. | |
| 6,096,924 A | 8/2000 | Studer et al. | |
| 6,140,528 A | 10/2000 | Hawkins | |
| 6,156,800 A | 12/2000 | Weichert | |
| 6,958,415 B2 | 10/2005 | Lal et al. | |
| 7,015,176 B2 | 3/2006 | Bailey et al. | |
| 7,126,026 B2* | 10/2006 | Schubert et al. | 564/162 |
| 7,375,138 B2* | 5/2008 | Kleemann | 514/618 |
| 7,449,594 B2* | 11/2008 | Schubert et al. | 558/415 |
| 2005/0202973 A1 | 9/2005 | Schaetzer et al. | |
| 2005/0215785 A1 | 9/2005 | Taylor | |

FOREIGN PATENT DOCUMENTS

| | | |
|---|---|---|
| DE | 10220549 | 12/2002 |
| DE | 10260474 | 7/2003 |
| WO | WO94/21606 | 9/1994 |
| WO | WO 01/30761 | 5/2001 |
| WO | WO 01/53256 | 7/2001 |
| WO | WO02/28182 | 4/2002 |
| WO | WO2005/019377 | 3/2005 |
| WO | WO2005/019378 | 3/2005 |
| WO | WO2005/021488 | 3/2005 |
| WO | WO2005/051390 | 6/2005 |

OTHER PUBLICATIONS

"NIH Heart Disease & Stroke Research: Fact Sheet" (American Heart Association, 2004.*
Cardiovascular Disease: Treatment for Stroke, Stanford Hospital & Clinics, 2003.*
Acute Congestive Heart Failure, Thomas N. Levin, Postgraduate Medicine, vol. 101, No. 1, 1997.*
Cecil Textbook of Medicine, 20th Edition, 1987.*
Doyle, M. et.al., Alkyl Nitrite-Metal Halide Deamination Reactions. 2. Substitutive Deamination of Arylamine by Alkyl Nitrites and Copper(II) Halides. A Direct and Remarkably Efficient Conversion of Arylamines to Aryl Halides1, J. Org. Chem. 1977, vol. 42, pp. 2426-2430.
Hassan, J. , Aryl-Aryl Bond Formation One Century after the Discovery of the Ullmann Reaction, Chem. Rev. 2002, 102, pp. 1359-1469.
Kirchhoff, et. al., Boronic Acids: New Coupling Partners in Room-Temperature Suzuki Reactions of Alkyl Bromides. Crystallographic Characterization of an Oxidative-Addition Adduct Generated Under remarkably Mild Conditions, J. Am. Chem. Soc. 2002 vol. 124, pp. 13662-13663.

(Continued)

Primary Examiner—Shailendra Kumar
(74) Attorney, Agent, or Firm—James W. Bolcsak

(57) ABSTRACT

Pentafluorosulfanylbenzoylguanidines of formula I

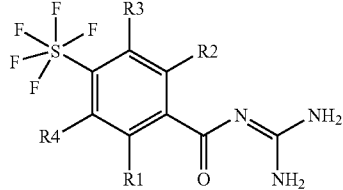

wherein R1 to R4 have the meanings stated in the claims, are suitable, for example, as antiarrhythmic medicaments with a cardioprotective component for the prophylaxis of infarction and treatment of infarction and for the treatment of angina pectoris. They also inhibit preventively the pathophysiological processes associated with the development of ischemia-induced damage, especially in the triggering of ischemia-induced cardiac arrhythmias.

11 Claims, 1 Drawing Sheet

OTHER PUBLICATIONS

Larock, R, Comprehensive Organic Transformations: A Guide to Functional Group Preparations Second Edition, Wiley-VCH Publishers, New York, Weinheim 1999, pp. 821-828.

Larock, R., Comprehensive Organic Transformations: A Guide to Functional Group Preparations Second Edition, Wiley-VCH Publishers, New York, Weinheim 1999, pp. 619-628.

Larock, R. et. al., Comprehensive Organic Transformations: A Guide to Functional Preparations Second Edition, Wiley-VCH Publishers, New York, Weinheim, 1999 pp. 1978-1986.

Larock, R.C. et. al, Comprehensive Organic Transformations: A Guide to Functional Group Preparations Second Edition, Wiley-VCH Publishers, New York, Weinheim, 1999, pp. 678-679.

Levin, T. H., et. al., Acute Congestive Heart Failure, Postgraduate Medicine, vol. 101, No. 1, (1997).

Miyaura, Norio et al., Palladium-Catalyzed Cross-Coupling Reactions of Organoboron Compounds, Chem Review, 1995, 95, (7), pp. 2457-2483.

March, J. et. al., Advanced Organic Chemistry: Reactions, Mechanisms, and Structure Third Edition, John Wiley & Sons 1985, pp. 348-351.

Netherton, M. et., al., Room-Temperature Alkyl-Alkyl Suzuki Cross-Coupling of Alkyl Bromides that Possess B Hydrogens, J. Am. Chem. Soc. 2001, 123, pp. 10099-10100.

Oae, S, et. al., Direct Conversion of Arylamines to the Halides by Deamination with Thionitrite or Related Compounds and Anhydrous Copper(II) Halides , Bull. Chem. Soc. Jpn. 1980, vol. 53, 1065-1069.

Simone, Oncology: Introduction, Cecil Textbook of Medicine, 20th Edition, vol. 1, 1996, pp. 1004-1010.

Smith, M.B. et. al., March's Advanced Organic Chemistry: Reactions, Mechanisms, and Structure, Wiley, New York, 2001, pp, 935-936.

Smith, M.B. et. al., March's Advanced Organice Chemistry: Reactions, Mechanisms, and Structure , Wiley, New York, 2001, pp. 1179-1180.

Smith, M.B. et.al., March's Advanced Organic Transformations: Reactions, Mechanisms, and Structure, Wiley, New York, 2001, pp. 704-707.

Stanforth, Stephen P., Catalytic Cross-coupling Reactions in Biaryl Synthesis, Tetrahedron, 54, (3/3), 1998, pp. 263-303.

Cardiovascular Disease: Treatment for Stroke, Stanford Hospital & Clinics; 2003.

NIH heart disease & stroke Research: Fact Sheet, American Heart Assoc., 2004.

* cited by examiner

PENTAFLUOROSULFANYLBENZOYL GUANIDINES, PROCESS FOR THEIR PREPARATION, USE AS A MEDICAMENT OR DIAGNOSTIC AID, AND MEDICAMENT COMPRISING SAME

RELATED APPLICATIONS

This application claims the benefit of foreign priority under 35 U.S.C. §119 of German patent application No. 10353202.1, filed on Nov. 13, 2003, the contents of which are incorporated by reference herein. This application is a CON of Ser. No. 10/989,069, filed Nov. 15, 2004, now abandoned, also claims the benefit of priority under 35 U.S.C. § 119(e) of U.S. Provisional Application No. 60/555,492, filed Mar. 23, 2004, the contents of which are incorporated by reference herein.

FIELD OF THE INVENTION

The present invention relates to substituted acylguanidines. In particular, the present invention relates to the use of pentafluorosulfanylbenzoylguanidines as inhibitors of cellular sodium-proton antiporter (Na+/H+ exchanger, NHE) and, thus, for treating diseases that are characteristic of NHE activity.

SUMMARY OF THE INVENTION

According to the present invention, compounds useful as NHE inhibitors include pentafluorosulfanylbenzoylguanidines compounds according to formula I:

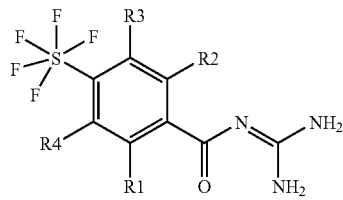

wherein R1 is hydrogen, alkyl having 1, 2, 3 or 4 carbon atoms, alkoxy having 1, 2, 3 or 4 carbon atoms, F, Cl, Br, I, —CN, NR5R6, —$O_p$—$(CH_2)_n$—$(CF_2)_o$—$CF_3$ or —$(SO_m)_q$—$(CH_2)_r$—$(CF_2)_s$—$CF_3$;

R5 and R6 are, independently of one another, hydrogen, alkyl having 1, 2, 3 or 4 carbon atoms or —$CH_2$—$CF_3$;

m is zero, 1 or 2;

n, o, p, q, r and s are, independently of one another, zero or 1;

R2 is hydrogen, alkyl having 1, 2, 3 or 4 carbon atoms, alkoxy having 1, 2, 3 or 4 carbon atoms, F, Cl, Br, I, —CN, NR7R8, —$O_t$—$(CH_2)_u$—$(CF_2)_n$—$CF_3$ or —$(SO_w)_x$—$(CH_2)_y$—$(CF_2)_z$—$CF_3$;

R7 and R8 are, independently of one another, hydrogen, alkyl having 1, 2, 3 or 4 carbon atoms, or —$CH_2$—$CF_3$;

w is zero, 1 or 2;

t, u, v, x, y and z are, independently of one another, zero or 1;

R3 is Cl, Br, I, —CN, —$SO_2CH_3$, alkoxy having 1, 2, 3 or 4 carbon atoms, NR9R10, —$O_a$—$(CH_2)_b$—$(CF_2)_c$—$CF_3$, $(SO_d)_e$—$(CH_2)_f$—$(CF_2)_g$—$CF_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be replaced by fluorine atoms;

R9 and R10 are, independently of one another, hydrogen, alkyl having 1, 2, 3 or 4 carbon atoms, or —$CH_2$—$CF_3$;

a, b and c are, independently of one another, zero or 1;

d is zero, 1 or 2;

e is zero or 1;

f is zero, 1, 2, 3 or 4;

g is zero or 1;

or R3 is —$(CH_2)_h$-phenyl or —O-phenyl, in which the phenyl radicals are unsubstituted or substituted by 1, 2 or 3 radicals selected from the group consisting of F, Cl, Br, I, —$O_j$—$(CH_2)_k$—$CF_3$, alkoxy having 1, 2, 3 or 4 carbon atoms, alkyl having 1, 2, 3 or 4 carbon atoms, and —$SO_2CH_3$;

j is zero or 1;

k is zero, 1, 2 or 3;

h is zero, 1, 2, 3 or 4;

or R3 is —$(CH_2)_{aa}$-heteroaryl, which is unsubstituted or substituted by 1, 2 or 3 radicals selected from the group consisting of F, Cl, Br, I, —$O_{bb}$—$(CH_2)_{cc}$—$CF_3$, alkoxy having 1, 2, 3 or 4 carbon atoms, alkyl having 1, 2, 3 or 4 carbon atoms, and —$SO_2CH_3$;

bb is zero or 1;

cc is zero or 1, 2 or 3;

aa is zero, 1, 2, 3 or 4;

R4 is hydrogen, F, Cl, Br, I, —CN, —$SO_2CH_3$, alkoxy having 1, 2, 3 or 4 carbon atoms, NR11R12, —$O_{dd}$—$(CH_2)_{ee}$—$(CF_2)_{ff}$—$CF_3$; —$(SO_{gg})_{hh}$—$(CH_2)_{jj}$—$(CF_2)_{kk}$—$CF_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be substituted by fluorine atoms;

R11 and R12 are, independently of one another, hydrogen, alkyl having 1, 2, 3 or 4 carbon atoms or —CH2—CF3;

dd, ee and ff are, independently of one another, zero or 1;

gg is zero, 1 or 2;

hh is zero or 1;

jj is zero, 1, 2, 3 or 4;

kk is zero or 1;

or R4 is —$(CH_2)_{ll}$-phenyl or —O-phenyl, wherein the phenyl radicals are unsubstituted or substituted by 1, 2 or 3 radicals selected from the group consisting of F, Cl, Br, I, —$O_{mm}$—$(CH_2)_{nn}$—$CF_3$, alkoxy having 1, 2, 3 or 4 carbon atoms, alkyl having 1, 2, 3 or 4 carbon atoms, and —$SO_2CH_3$;

mm is zero or 1;

nn is zero, 1, 2 or 3;

ll is zero, 1, 2, 3 or 4;

or R4 is —$(CH_2)_{ll}$-heteroaryl, which is unsubstituted or substituted by 1, 2 or 3 radicals selected from the group consisting of F, Cl, Br, I, —$O_{pp}$—$(CH_2)$, —$CF_3$, alkoxy having 1, 2, 3 or 4 carbon atoms, alkyl having 1, 2, 3 or 4 carbon atoms, and —$SO_2CH_3$;

pp is zero or 1;

rr is zero, 1, 2 or 3; and oo is zero, 1, 2, 3 or 4, and the pharmaceutically acceptable salts thereof.

In another aspect of the present invention, the compounds of formula I and the pharmaceutically acceptable salts thereof are suitable for the prevention and treatment of diseases caused by activation or activated NHE, and of diseases caused secondarily by the NHE-related damage.

Compared with known compounds, the compounds of the present invention are distinguished by an extremely high activity in the inhibition of Na+/H+ exchange, and by improved ADMET properties (adsorption, distribution, metabolism, excretion, and toxicology). The xenobiotic structure (in particular the introduction of the rather "unnatural/manmade" $SF_5$ substituents) advantageously influences tissue distribution. This leads inter alia to increased exposures in vivo. This involves no significant influence on the absorption characteristics, and the high bioavailability of the acylguanidines is retained. In contrast to some acylguanidines described in the literature, the compounds of formula I described herein and their pharmaceutically acceptable salts show no unwanted and disadvantageous saliduretic properties.

BRIEF DESCRIPTION OF THE DRAWINGS

The present invention will be further understood from the following description with reference to the drawings, in which.

DETAILED DESCRIPTION OF THE INVENTION

Figure 1:
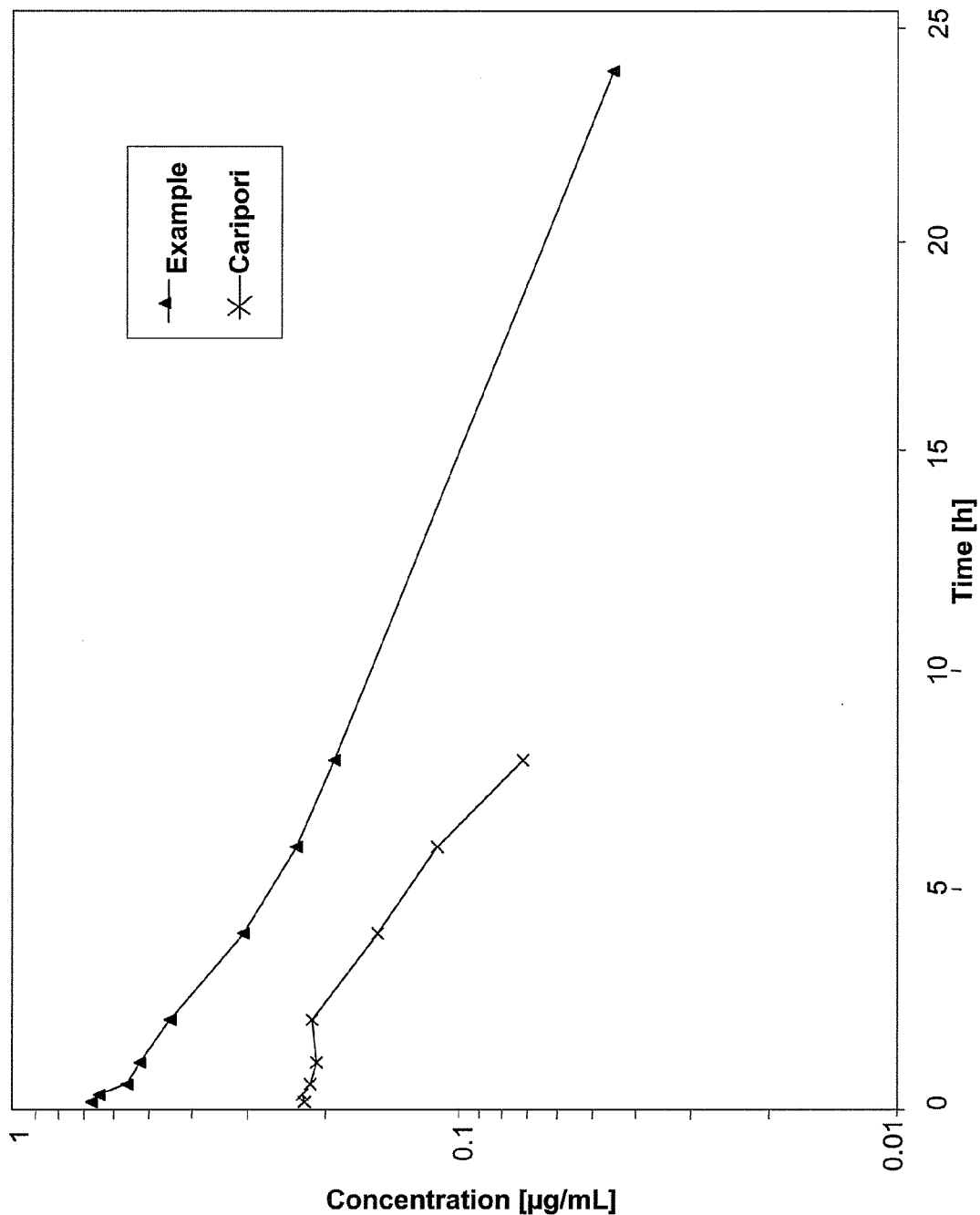
FIG. 1 shows concentration-time plots of compounds according to the present invention in the blood plasma of dogs.

According to the present invention, compounds useful as NHE inhibitors include pentafluorosulfanylbenzoylguanidines compounds according to formula I:

I wherein R1 is hydrogen, alkyl having 1, 2, 3 or 4 carbon atoms, alkoxy having 1, 2, 3 or 4 carbon atoms, F, Cl, Br, I, —CN, NR5R6, —$O_p$—$(CH_2)_n$—$(CF_2)_o$—$CF_3$ or —$(SO_m)_q$—$(CH_2)_r$—$(CF_2)_s$—$CF_3$;

R5 and R6 are, independently of one another, hydrogen, alkyl having 1, 2, 3 or 4 carbon atoms or —$CH_2$—$CF_3$;

m is zero, 1 or 2;

n, o, p, q, r and s are, independently of one another, zero or 1;

R2 is hydrogen, alkyl having 1, 2, 3 or 4 carbon atoms, alkoxy having 1, 2, 3 or 4 carbon atoms, F, Cl, Br, I, —CN, NR7R8, —$O_t$—$(CH_2)_u$—$(CF_2)_v$—$CF_3$ or —$(SO_w)_x$—$(CH_2)_y$—$(CF_2)_z$—$CF_3$;

R7 and R8 are, independently of one another, hydrogen, alkyl having 1, 2, 3 or 4 carbon atoms, or —$CH_2$—$CF_3$;

w is zero, 1 or 2;

t, u, v, x, y and z are, independently of one another, zero or 1;

R3 is Cl, Br, I, —CN, —$SO_2CH_3$, alkoxy having 1, 2, 3 or 4 carbon atoms, NR9R10, —$O_a$—$(CH_2)_b$—$(CF_2)_c$—$CF_3$, —$(SO_d)_e$—$(CH_2)_f$—$(CF_2)_g$—$CF_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be replaced by fluorine atoms;

R9 and R10 are, independently of one another, hydrogen, alkyl having 1, 2, 3 or 4 carbon atoms, or —$CH_2$—$CF_3$;

a, b and c are, independently of one another, zero or 1;

d is zero, 1 or 2;

e is zero or 1;

f is zero, 1, 2, 3 or 4;

g is zero or 1;

or R3 is —$(CH_2)_h$-phenyl or —O-phenyl, in which the phenyl radicals are unsubstituted or substituted by 1, 2 or 3 radicals selected from the group consisting of F, Cl, Br, I, —$O_j$—$(CH_2)_k$—$CF_3$, alkoxy having 1, 2, 3 or 4 carbon atoms, alkyl having 1, 2, 3 or 4 carbon atoms, and —$SO_2CH_3$;

j is zero or 1;

k is zero, 1, 2 or 3;

h is zero, 1, 2, 3 or 4;

or R3 is —$(CH_2)_{aa}$-heteroaryl, which is unsubstituted or substituted by 1, 2 or 3 radicals selected from the group consisting of F, Cl, Br, I, —$O_{bb}$—$(CH_2)_{cc}$—$CF_3$, alkoxy having 1, 2, 3 or 4 carbon atoms, alkyl having 1, 2, 3 or 4 carbon atoms, and —$SO_2CH_3$;

bb is zero or 1;

cc is zero or 1, 2 or 3;

aa is zero, 1, 2, 3 or 4;

R4 is hydrogen, F, Cl, Br, I, —CN, —$SO_2CH_3$, alkoxy having 1, 2, 3 or 4 carbon atoms, NR11R12, —$O_{dd}$—$(CH_2)_{ee}$—$(CF_2)_{ff}$—$CF_3$; —$(SO_{gg})_{hh}$—$(CH_2)_{ii}$—$(CF_2)_{kk}$—$CF_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be substituted by fluorine atoms;

R11 and R12 are, independently of one another, hydrogen, alkyl having 1, 2, 3 or 4 carbon atoms or —$CH2$—$CF3$;

dd, ee and ff are, independently of one another, zero or 1;

gg is zero, 1 or 2;

hh is zero or 1;

ii is zero, 1, 2, 3 or 4;

kk is zero or 1;

or R4 is —$(CH_2)_{ll}$-phenyl or —O-phenyl, wherein the phenyl radicals are unsubstituted or substituted by 1, 2 or 3 radicals selected from the group consisting of F, Cl, Br, I, —$O_{mm}$—$(CH_2)_{nn}$—$CF_3$, alkoxy having 1, 2, 3 or 4 carbon atoms, alkyl having 1, 2, 3 or 4 carbon atoms, and —$SO_2CH_3$;

mm is zero or 1;

nn is zero, 1, 2 or 3;

ll is zero, 1, 2, 3 or 4;

or R4 is —$(CH_2)_{oo}$-heteroaryl, which is unsubstituted or substituted by 1, 2 or 3 radicals selected from the group consisting of F, Cl, Br, I, —$O_{pp}$—$(CH_2)_{rr}$$CF_3$, alkoxy having 1, 2, 3 or 4 carbon atoms, alkyl having 1, 2, 3 or 4 carbon atoms, and —$SO_2CH_3$;

pp is zero or 1;

rr is zero, 1, 2 or 3; and oo is zero, 1, 2, 3 or 4, and the pharmaceutically acceptable salts thereof.

In one embodiment of the present invention, preferred compounds include compounds of formula I, wherein R1 is hydrogen, alkyl having 1, 2, 3 or 4 carbon atoms, alkoxy having 1, 2, 3 or 4 carbon atoms, F, Cl, Br, I, —CN, NR5R6, —$O_p$—$(CH_2)_n$—$(CF_2)_o$—$CF_3$ or —$(SO_m)_q$—$(CH_2)_r$—$(CF_2)_s$—$CF_3$;

R5 and R6 are, independently of one another, hydrogen, alkyl having 1, 2, 3 or 4 carbon atoms, or —$CH_2$—$CF_3$;

m is zero, 1 or 2;

n, o, p, q, r and s are, independently of one another, zero or 1;

R2 is hydrogen or F;

R3 is Cl, Br, I, —CN, —$SO_2CH_3$, alkoxy having 1, 2, 3 or 4 carbon atoms, NR9R10, —$O_a$—$(CH_2)_b$—$(CF_2)_c$—$CF_3$, —$(SO_d)_e$—$(CH_2)_f$—$(CF_2)_g$—$CF_3$, alkyl having 1, 2, 3, 4, 5 or 6 carbon atoms, or cycloalkyl having 3, 4, 5, 6, 7 or 8 carbon atoms, wherein 1, 2, 3 or 4 hydrogen atoms may be replaced by fluorine atoms;

R9 and R10 are, independently of one another, hydrogen, alkyl having 1, 2, 3 or 4 carbon atoms, or $-CH_2-CF_3$;

a, b and c are, independently of one another, zero or 1;

d is zero, 1 or 2;

e is zero or 1;

f is zero, 1, 2, 3 or 4;

g is zero or 1;

or R3—$(CH_2)_h$-phenyl or —O-phenyl, wherein the phenyl radicals are unsubstituted or substituted by 1, 2 or 3 radicals selected from the group consisting of F, Cl, Br, I, $-O_j-(CH_2)_k-CF_3$, alkoxy having 1, 2, 3 or 4 carbon atoms, alkyl having 1, 2, 3 or 4 carbon atoms, and $-SO_2CH_3$;

j is zero or 1;

k is zero, 1, 2 or 3;

h is zero, 1, 2, 3 or 4;

or R3—$(CH_2)_{aa}$-heteroaryl, which is unsubstituted or substituted by 1, 2 or 3 radicals selected from the group consisting of F, Cl, Br, I, $-O_{bb}-(CH_2)_{cc}-CF_3$, alkoxy having 1, 2, 3 or 4 carbon atoms, alkyl having 1, 2, 3 or 4 carbon atoms, and $-SO_2CH_3$;

bb is zero or 1;

cc is zero, 1, 2 or 3;

aa zero, 1, 2, 3 or 4; and

R4 is hydrogen or F, and the pharmaceutically acceptable salts thereof.

In a particularly preferred embodiment of the present invention, compounds of formula I include compounds wherein R1 is hydrogen, alkyl having 1, 2, 3 or 4 carbon atoms, alkoxy having 1, 2, 3 or 4 carbon atoms, F, Cl, Br, I, —CN, NR5R6, $-O-CH_2-CF_3$, or $-(SO_m)_q-(CH_2)_r-CF_3$;

R5 and R6 are, independently of one another, hydrogen, alkyl having 1, 2, 3 or 4 carbon atoms, or $-CH_2-CF_3$;

m is zero, 1 or 2;

q and r are, independently of one another, zero or 1;

R2 is hydrogen or F;

R3 is Cl, Br, I, —CN, $-SO_2CH_3$, alkoxy having 1, 2, 3 or 4 carbon atoms, NR9R10, $-O-CH_2-CF_3$, $-(SO_d)_e-CF_3$, alkyl having 1, 2, 3, 4, 5 or 6 carbon atoms, or cycloalkyl having 3, 4, 5, 6, 7 or 8 carbon atoms, wherein 1, 2, 3 or 4 hydrogen atoms may be replaced by fluorine atoms;

R9 and R10 are, independently of one another, hydrogen, alkyl having 1, 2, 3 or 4 carbon atoms, or $-CH_2-CF_3$;

d is zero, 1 or 2;

e is zero or 1;

or R3 is phenyl, which is unsubstituted or substituted by 1, 2 or 3 radicals selected from the group consisting of F, Cl, Br, I, $-O_j-(CH_2)_k-CF_3$, alkoxy having 1, 2, 3 or 4 carbon atoms, alkyl having 1, 2, 3 or 4 carbon atoms, and $-SO_2CH_3$;

zero or 1;

k is zero, 1, 2 or 3;

or R3 is heteroaryl, which is unsubstituted or substituted by 1, 2 or 3 radicals selected from the group consisting of F, Cl, Br, I, $-O_{bb}-(CH_2)_{cc}-CF_3$, alkoxy having 1, 2, 3 or 4 carbon atoms, alkyl having 1, 2, 3 or 4 carbon atoms, and $-SO_2CH_3$;

bb is zero or 1;

cc is zero, 1, 2 or 3; an

R4 is hydrogen or F, and the pharmaceutically acceptable salts thereof. According to another embodiment of the invention, very particularly preferred compounds include compounds of formula I wherein R1 is hydrogen, alkyl having 1, 2, 3 or 4 carbon atoms, methoxy, ethoxy, F, Cl, NR5R6, $-O-CH_2-CF_3$, or $-(SO_m)_q-(CH_2)_r-CF_3$;

R5 and R6 are, independently of one another, hydrogen, alkyl having 1, 2, 3 or 4 carbon atoms, or $-CH_2-CF_3$;

m is zero, 1 or 2;

q and r are, independently of one another, zero or 1;

R2 is hydrogen or F;

R3 is Cl, —CN, $-SO_2CH_3$, methoxy, ethoxy, NR9R10, $-O-CH_2-CF_3$, $-(SO_d)_e-CF_3$, alkyl having 1, 2, 3, 4, 5 or 6 carbon atoms, or cycloalkyl having 3, 4, 5, 6 or 7 carbon atoms, wherein 1, 2, 3 or 4 hydrogen atoms may be replaced by fluorine atoms;

R9 and R10 are, independently of one another, hydrogen, methyl, ethyl or $-CH_2-CF_3$;

d is zero, 1 or 2;

e is zero or 1;

or R3 is phenyl, which is unsubstituted or substituted by 1 or 2 radicals selected from the group consisting of F, Cl, $-O_j-(CH_2)_k-CF_3$, methoxy, ethoxy, alkyl having 1, 2, 3 or 4 carbon atoms, and $-SO_2CH_3$;

j and k are, independently of one another, zero or 1;

or R3 is heteroaryl, which is unsubstituted or substituted by 1 or 2 radicals selected from the group consisting of F, Cl, $-O_{bb}-(CH_2)_{cc}-CF_3$, methoxy, ethoxy, alkyl having 1, 2, 3 or 4 carbon atoms, and $-SO_2CH_3$;

bb and cc are, independently of one another, zero or 1; and

R4 is hydrogen or F, and the pharmaceutically acceptable salts thereof.

In yet another embodiment of the present invention, preferred compounds of formula I include those wherein R1 is hydrogen, alkyl having 1, 2, 3 or 4 carbon atoms, alkoxy having 1, 2, 3 or 4 carbon atoms, F, Cl, Br, I, —CN, NR5R6, where R5 and R6 are, independently of one another, hydrogen, alkyl having 1, 2, 3 or 4 carbon atoms or $-CH_2-CF_3$, or $-O-CH_2-CF_3$ or $-(SO_m)_q-(CH_2)_r-CF_3$, where m is zero, 1 or 2, and q and r are, independently of one another, are zero or 1. Particularly preferred compounds of formula I include compounds wherein R1 is hydrogen, alkyl having 1, 2, 3 or 4 carbon atoms, methoxy, ethoxy, F, Cl, NR5R6, where R5 and R6, are independently of one another, hydrogen, alkyl having 1, 2, 3, or 4 carbon atoms or $-CH_2-CF_3$, $-O-CH_2-CF_3$ or $-(SO_m)_q-(CH_2)_r-CF_3$, where m is zero, 1 or 2, and q and r are, independently of one another, zero or 1. More particularly preferred compounds of formula I include compounds wherein R1 is hydrogen, methyl, ethyl, $CF_3-CH_2-O-$, F, Cl or $CF_3$. Still more particularly preferred compounds of formula I include compounds wherein R1 is hydrogen, methyl or ethyl, and is, preferably, methyl or ethyl.

In yet another embodiment of the present invention, preferred compounds of formula I include those wherein R2 is hydrogen or F. Particularly preferred compounds of formula I include compounds wherein R2 is hydrogen.

In still another embodiment of the present invention, preferred compounds of formula I include those wherein R3 is Cl, —CN, $-SO_2CH_3$, methoxy, ethoxy, NR9R10 (where R9 and R10 are, independently of one another, hydrogen, methyl, ethyl or $-CH_2-CF_3$, or $-O-CH_2-CF_3$, $-(SO_d)_e-CF_3$, wherein d is zero, 1 or 2, and e is zero or 1), alkyl having 1, 2, 3, 4, 5 or 6 carbon atoms or cycloalkyl having 3, 4, 5, 6 or 7 carbon atoms (wherein 1, 2, 3 or 4 hydrogen atoms may be replaced by fluorine atoms), phenyl which is unsubstituted or substituted by 1, 2 or 3 radicals selected from the group consisting of F, Cl, Br, I, $-O_j-(CH_2)_k-CF_3$ (wherein j is zero or 1 and k is zero, 1, 2 or 3), alkoxy having 1, 2, 3 or 4 carbon atoms, alkyl having 1, 2, 3 or 4 carbon atoms, $-SO_2CH_3$, or heteroaryl which is unsubstituted or substituted by 1, 2 or 3 radicals selected from the group consisting of F, Cl, Br, I, $-O_{bb}-(CH_2)_{cc}-CF_3$ (where bb is zero or 1 and cc is zero, 1, 2 or 3). Particularly preferred compounds of formula I include compounds wherein R3 is Cl, —CN, —SO₂CH₃, methoxy, ethoxy, NR9R10 (where R9 and R10 are, independently of one another, hydrogen, methyl, ethyl or —CH₂—CF₃, or —O—CH₂—CF₃, —(SO$_d$)$_e$—CF₃, wherein d is zero, 1 or 2, and e is zero or 1), alkyl having 1, 2, 3, 4, 5 or 6 carbon atoms or cycloalkyl having 3, 4, 5, 6 or 7 carbon atoms (wherein 1, 2, 3 or 4 hydrogen atoms may be replaced by fluorine atoms), phenyl which is unsubstituted or substituted by 1-2 radicals selected from the group consisting of F, Cl, —O$_j$—(CH₂)$_k$—CF₃ (where j and k are, independently of one another, zero or 1), methoxy, ethoxy, alkyl having 1, 2, 3 or 4 carbon atoms and —SO₂CH₃, or heteroaryl which is unsubstituted or substituted by 1-2 radicals selected from the group consisting of F, Cl, —O$_{bb}$—(CH₂)$_{cc}$—CF₃ (where bb and cc are, independently of one another, zero or 1). More particularly preferred compounds of formula I include compounds wherein R3 is Cl, —CN or —SO₂CH₃.

In another embodiment of the present invention, preferred compounds of formula I include those wherein R4 is hydrogen and F. Particularly preferred compounds of formula I include compounds wherein R4 is hydrogen.

In another embodiment of the present invention, preferred compounds of formula I include those wherein p, t, a, and dd are, independently of one another, 1.

If the substituents R1 to R4 contain one or more centers of asymmetry, these may independently of one another have both the S and the R configuration. The compounds may be in the form of optical isomers, of diastereomers, of racemates or of mixtures thereof.

The present invention encompasses all tautomeric forms of the compounds of formula I.

According to the present invention, alkyl radicals may be straight-chain or branched. This also applies if they carry substituents or occur as substituents of other radicals, for example in fluoroalkyl radicals or alkoxy radicals. Examples of alkyl radicals include methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals include methyl, ethyl, n-propyl and isopropyl. One or more, for example 1, 2, 3, 4 or 5, hydrogen atoms in alkyl radicals may be replaced by fluorine atoms. Examples of such fluoroalkyl radicals include trifluoromethyl, 2,2,2-trifluoroethyl and pentafluoroethyl. Substituted alkyl radicals may be substituted in any positions. Examples of cycloalkyl radicals include cyclopropyl, cyclobutyl, cyclopentyl, cyclohexyl, cycloheptyl or cyclooctyl. One or more, for example 1, 2, 3 or 4, hydrogen atoms in cycloalkyl radicals may be replaced by fluorine atoms. Substituted cycloalkyl radicals may be substituted in any positions.

Phenyl radicals may be unsubstituted or be substituted one or more times, for example once, twice or three times, by identical or different radicals. If a phenyl radical is substituted, it preferably has one or two identical or different substituents. This likewise applies to substituted phenyl radicals in groups such as, for example, phenylalkyl or phenyloxy. The substituent in monosubstituted phenyl radicals may be in position 2, position 3 or position 4. Disubstituted phenyl may be substituted in the 2,3 position, 2,4 position, 2,5 position, 2,6 position, 3,4 position or 3,5 position. The substituents in trisubstituted phenyl radicals may be in the 2,3,4 position, 2,3,5 position, 2,4,5 position, 2,4,6 position, 2,3,6 position or 3,4,5 position.

Heteroaryl radicals are aromatic ring compounds in which one or more ring atoms are oxygen atoms, sulfur atoms or nitrogen atoms, e.g., 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or be substituted one or more times, for example once, twice or three times, by identical or different radicals. This applies likewise to heteroaryl radicals such as, for example, in the radical heteroarylalkyl. Examples of heteroaryl include furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Further examples of heteroaryl radicals include, in particular, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also encompassed are the corresponding N-oxides of these compounds, i.e., for example 1-oxy-2-, 3- or 4-pyridyl.

Particularly preferred heteroaromatic radicals include 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

The invention further relates to a process for preparing the compounds of formula I which comprises reacting a compound of formula II

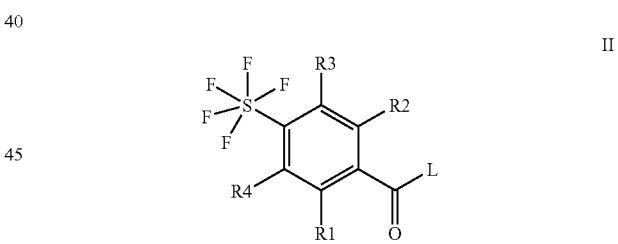

in which R1 to R4 are as previously defined, and L is a leaving group which can undergo nucleophilic substitution, with guanidine.

The activated acid derivatives of formula II in which L is an alkoxy, preferably a methoxy, group, a phenoxy group, phenylthio, methylthio, 2-pyridylthio group, a nitrogen heterocycle, preferably 1-imidazolyl, are typically obtained in a manner known to those skilled in the art from the underlying carbonyl chlorides (formula II; L=Cl), which in turn can themselves be prepared in a known manner from the underlying carboxylic acids (formula II; L=OH), for example using thionyl chloride.

Besides the carbonyl chlorides of formula II (L=Cl), it is also possible to prepare other activated acid derivatives of formula II in a known manner directly from the underlying benzoic acids (formula II; L=OH), such as the methyl esters of formula II with L=OCH₃, by treatment with gaseous HCl in methanol, the imidazolides of formula II by treatment with carbonyldiimidazole, the mixed anhydrides of formula II by treatment with Cl—COOC$_2$H$_5$ or tosyl chloride in the presence of triethylamine in an inert solvent, as activations of benzoic acids with dicyclohexylcarbodiimide (DCC) or with O-[(cyano(ethoxycarbonyl)methylene)amino]-1,1,3,3-tetramethyluronium tetrafluoroborate ("TOTU") are also possible. A number of suitable methods for preparing activated carboxylic acid derivatives of formula II are indicated in J. March, Advanced Organic Chemistry, third edition (John Wiley & Sons, 1985, page 350), indicating source literature.

Reaction of an activated carboxylic acid derivative of formula II with guanidine preferably takes place in a known manner in a protic or aprotic polar but inert organic solvent. Those that have proved suitable for the reaction of the methyl benzoates (formula II; L=OCH$_3$) with guanidine are methanol, isopropanol or THF at temperatures from 20° C. to the boiling point of these solvents. Most reactions of compounds of formula II with salt-free guanidine are, for example, carried out in aprotic inert solvents such as THF, dimethoxyethane, dioxane. However, it is also possible to use water in the presence of a base such as, for example, NaOH as solvent in the reaction of compounds of formula II with guanidine.

If L is Cl, it is advantageous to add an acid scavenger, for example in the form of excess guanidine, to bind the hydrohalic acid.

The compounds of formula II can be prepared as follows, by

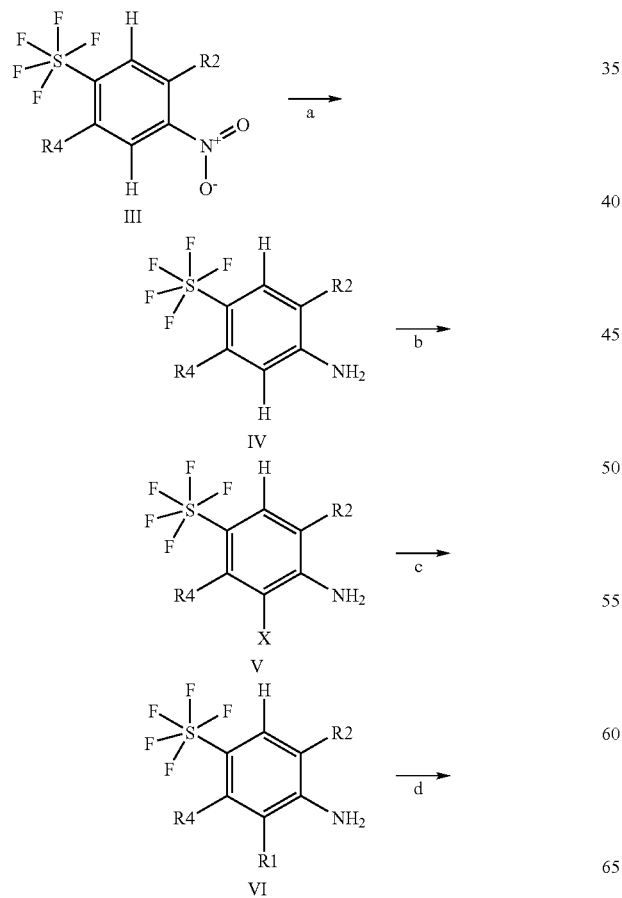

a) reducing a 4-nitrophenylsulfurpentafluoride derivative of formula III to the amine of formula IV;

b) halogenating the compound of formula IV in the ortho position to the amino group with a halogenating agent to give the compound of formula V;

c) replacing the halogen substituent in the compound of formula V with a suitable nucleophile or an organoelement compound, for example an alkylboron compound, where appropriate with catalysis, by a substituent R1;

d) replacing the amino function in the compound of formula VI by a halogen substituent;

e) replacing the halogen substituent in the compound of formula VII by a nitrile function;

f) hydrolyzing the nitrile function of the compound of formula VIII to the carboxylic acid;

g) nitrating the compound of formula IX in the ortho position to the pentafluorosulfanyl group to give the compound of formula X;

h) reducing the nitro compound of formula X to the aniline;

i) replacing the amino function in the compound of formula XI by R3 using a suitable nucleophile; and k) converting the compound of formula XII into the compound of formula II, wherein in the compounds of formulae II, m, IV, V, VI, VII, VIII, IX, X, XI and XII, R1 to R4 and L are as previously defined; and X and Y are, independently of one another, F, Cl, Br or I.

The procedure for preparing the compounds of formula II in step a is to initially convert the compounds of formula III by methods known in principle for the reduction of aromatic nitro compounds to aromatic amines into compounds of formula IV. Such methods are described, for example, in: R. C. Larock, Comprehensive Organic Transformations: A Guide to Functional Group Preparations, VCH Publishers, New York, Weinheim, 1999, 821-828 and the literature cited therein.

Subsequently in step b, the compounds of formula IV are dissolved in an organic solvent A and reacted with a halogenating agent such as, for example, a brominating agent. The reaction temperature in this case is generally from −30° C. to +150° C., preferably 0° C. to 40° C. The reaction time is generally from 10 min to 20 h, depending on the composition of the mixture and the chosen temperature range. The resulting reaction mixture can be worked up by subsequent filtration through a layer of silica gel, washing with organic solvent A and, after removal of the solvent in vacuo, purifying the product by conventional purification methods such as recrystallization, distillation or chromatography. Preferably, from 0.1 to 10 mol of the compound of formula IV, for example, are dissolved in 1000 ml of organic solvent A. Preferably, from 0.8 to 1.2 equivalents of the halogenating agent are used for 1 mol of the compound of formula IV to be halogenated.

As used herein, the term "halogenating agent" means a molecule capable of incorporating at least one halogen atom into a chemical compound or radical, for example, elemental halogens, halogen-amine complexes, cyclic and acyclic N-halogenated carboxamides and -imides, and ureas, as described, for example, in R. C. Larock, Comprehensive Organic Transformations: A Guide to Functional Group Preparations, VCH Publishers, New York, Weinheim, 1999, 619-628, and the literature cited therein or M. B. Smith and J. March, March's Advanced Organic Chemistry: Reactions, Mechanisms, and Structure, Wiley, New York, 2001, 704-707, and the literature cited therein. Examples of halogenating agents according to the present invention include N-bromosuccinimide, N-chlorosuccinimide, HBr in $H_2SO_4$ or 1,3-dibromo-5,5-dimethylimidazolidine-2,4-dione. As used herein, the term "brominating agent" means a halogenating agent, wherein the halogen is bromine, for example, elemental bromine, bromine-amine complexes, cyclic and acyclic N-brominated carboxamides and -imides, and ureas, as described, for example, in R. C. Larock, Comprehensive Organic Transformations: A Guide to Functional Group Preparations, VCH Publishers, New York, Weinheim, 1999, 622-624, and the literature cited therein or M. B. Smith and J. March, March's Advanced Organic Chemistry: Reactions, Mechanisms, and Structure, Wiley, New York, 2001, 704-707, and the literature cited therein. Brominating agents according to the present invention include, for example, N-bromosuccinimide, HBr in $H_2SO_4$ or 1,3-dibromo-5,5-dimethylimidazolidine-2,4-dione, the latter being able to transfer 2 bromine atoms per molecule.

As used herein, the term "organic solvent A" means aprotic solvents such as, for example, dichloromethane, chloroform, tetrachloromethane, pentane, hexane, heptane, octane, benzene, toluene, xylene, chlorobenzene, 1,2-dichloroethane, trichloroethylene or acetonitrile.

Organic or inorganic bases can trap any HX produced in the reaction.

In step c, the compounds of formula V are typically subsequently dissolved in an organic solvent B and reacted with a nucleophile $R1^{-1}$ or an element compound comprising the substituent R1 to give compounds of formula VI. It is possible in this case to add a base A and to add a catalyzing metal salt A.

The reaction temperature in this case is generally between −20° C. and +150° C., preferably between 30° C. and 100° C. The reaction time is generally from 0.5 h to 20 h, depending on the composition of the mixture and the chosen temperature range. The resulting reaction mixture can be worked up by subsequent filtration through a layer of silica gel, washing with an organic solvent B and, after removal of the solvent in vacuo, purifying the product by conventional purification processes such as recrystallization, chromatography, for example on silica gel, distillation or steam distillation.

From 0.1 to 10 mol of the compound of formula V, for example, are dissolved in 1000 ml of organic solvent B. Preferably, from 0.8 to 3 equivalents of the nucleophile $R1^-$ or of the element compound comprising the substituent R1 are used for 1 mol of the starting compound of formula V.

As used herein, the term "nucleophile $R1^-$" means compounds which result on deprotonation of a compound R1-H with strong bases such as, for example, alkyl- or aryllithium compounds, organomagnesium compounds, alcoholates or lithium diisopropylamide.

As used herein, the term "organoelement compounds comprising the substituent R1" means organolithium compounds R1-Li, organomagnesium compounds R1-Mg-Hal, with Hal=Cl, Br, I, organoboron compounds such as $R1-B(OH)_2$, R1-boronic esters such as, for example,

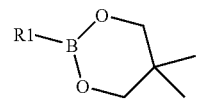

R1-boronic anhydrides such as, for example,

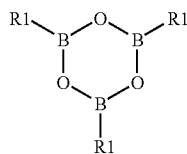

or organozinc compounds R1-Zn-Z, with Z=Cl, Br, I.

As used herein, the term "base A" means bases like those typically used as auxiliary bases in cross-coupling reactions and mentioned, for example, in A. Suzuki et al., Chem. Rev. 1995, 95, 2457-2483 or M. Lamaire et al., Chem. Rev. 2002, 102, 1359-1469 or S. P. Stanforth, Tetrahedron 1998, 54, 263-303 and the literature cited therein in each case, for example $Na_2CO_3$, $Cs_2CO_3$, KOH, NaOH, $K_3PO_4$, $N(ethyl)_3$.

As used herein, the term "organic solvent B." means protic or aprotic solvents such as diethyl ether, dimethoxyethane, THF, alcohols, water or mixtures thereof. In one embodiment, mixtures with water are preferred.

As used herein, the term "catalyzing metal salt A" means inter alia Pd and Ni catalysts like those used for Suzuki and Negishi reactions and described for example in A. Suzuki et al., Chem. Rev. 1995, 95, 2457-2483 or M. Lamaire et al., Chem. Rev. 2002, 102, 1359-1469 or S. P. Stanforth, Tetrahedron 1998, 54, 263 or G. C. Fu et al., J. Am. Chem. Soc. 2001, 123, 10099 or G. C. Fu et al., J. Am. Chem. Soc. 2002, 124, 13662 and the literature cited therein in each case, including the added ligands such as $Pd(OAc)_2$, $PdCl_2(dppf)$ or $Pd_2(dba)_3$.

In step d, the compounds of formula VI are subsequently converted into the compounds of formula VII by a diazotization-halogenation process with a diazotizing-halogenating agent such as, for example, a diazotizing-brominating agent as described for other aromatic amines to replace the amine function by a halogen function as detailed, for example, in M. B. Smith and J. March, March's Advanced Organic Chemistry: Reactions, Mechanisms, and Structure, Wiley, New York, 2001, 935-936 or R. C. Larock, Comprehensive Organic Transformations: A Guide to Functional Group Preparations, VCH Publishers, New York, Weinheim, 1999, 678-679 and the literature cited therein, such as, for example, the Sandmeyer or Gattermann reaction. The process of M. Doyle et al., J. Org. Chem. 1977, 42, 2426 or of S. Oae et al., Bull. Chem. Soc. Jpn. 1980, 53, 1065 is preferred.

In step e, the compounds of formula VII are reacted in a solvent C with a cyanidating agent such as, for example, with addition of a catalyzing metal salt B. The reaction temperature is generally from 20° C. to 200° C., in one embodiment of the present invention, it is preferably 80° C. to 150° C. The reaction time is typically from 1 h to 20 h, depending on the composition of the mixture and the chosen temperature range. The resulting reaction mixtures can be filtered with suction through a layer of silica gel, for example, and the filtrate can be worked up by aqueous extraction. After evaporation of the solvent in vacuo, the compound of formula VIII is purified by conventional purification processes such as, for example, recrystallization, chromatography on silica gel, distillation or steam distillation. From 0.1 to 10 mol of the compound of formula VII for example are dissolved in 1000 ml of organic solvent C. Preferably, from 1 to 10 equivalents of the cyanidating agent are used for 1 mol of the compounds having formula VII to be reacted.

As used herein, the term "cyanidating agent" means a molecule capable of introducing a cyano group into a compound or radical, for example, alkali metal cyanides or $Zn(CN)_2$ either alone or mixed with metallic zinc. In one embodiment of the present invention, the cyanidating agent is preferably mixed with zinc dust.

As used herein, the term "organic solvent C" preferably means aprotic polar solvents such as, for example, DMF, dimethylacetamide, NMP, DMSO.

As used herein, the term "catalyzing metal salt B" means inter alia Pd and Ni catalysts like those employed in Suzuki reactions and described for example in A. Suzuki et al., Chem. Rev. 1995, 95, 2457-2483 or M. Lamaire et al., Chem. Rev. 2002, 102, 1359-1469 or S. P. Stanforth, Tetrahedron 1998, 54, 263 and the literature cited therein, for example $PdCl_2$(dppf), $Pd(OAc)_2$, $Pd_2(dba)_3$.

The resulting compounds of formula VIII are subsequently hydrolyzed in step f to the carboxylic acids of formula IX, for example in the presence of a base. This can take place by processes known to the skilled worker for hydrolyzing aromatic nitriles, as described, for example, in R. C. Larock, Comprehensive Organic Transformations: A Guide to Functional Group Preparations, VCH Publishers, New York, Weinheim, 1999, 1986-1987 or M. B. Smith and J. March, March's Advanced Organic Chemistry: Reactions, Mechanisms, and Structure, Wiley, New York, 2001, 1179-1180 and the literature cited therein.

In step g, compounds of formula IX are nitrated with a nitrating agent as described, for example, in Houben-Weyl, Methoden der organischen Chemie 4th edition, Organo-Stickstoff-Verbindungen IV, part 1, Georg Thieme Verlag Stuttgart 1992, pages 262-341.

In step h, the nitro compounds of formula X are converted into compounds of formula XI by methods known in principle for reducing aromatic nitro compounds to aromatic amines. Such methods are described for example in: R. C. Larock, Comprehensive Organic Transformations: a Guide to Functional Group Preparations, VCH Publishers, New York, Weinheim, 1999, 821-828 and the literature cited therein.

In step i, the anilines of formula XI are converted by the diazotization-replacement route into the compounds of formula XII with replacement of the amine group by R3. Such methods are known to the skilled worker and are described for example in Houben-Weyl, Methoden der organischen Chemie 4th edition, Organo-Stickstoff-Verbindungen I, part 2, Georg Thieme Verlag Stuttgart 1990, pages 1087-1136 and the references cited therein. For example, an aniline of formula XI can be converted by the diazotization-replacement route into a sulfochloride of formula XII (R3=$SO_2Cl$) as described, for example, in Houben-Weyl, Methoden der organischen Chemie 4th edition, Organo-Schwefel-Verbindungen, part 2, Georg Thieme Verlag Stuttgart 1985, pages 1069-1070.

In step k, the compounds of formula XII are derivatized to the compounds of formula II by methods known to the skilled worker and as described above. It is possible in this step, for example, for the sulfochlorides of formula XII (R3=$SO_2Cl$) to be converted initially into the corresponding sulfinic acids (as described for example in Houben-Weyl, Methoden der organischen Chemie 4th edition, Organo-Schwefel-Verbindungen, part 1, Georg Thieme Verlag Stuttgart 1985, pages 620-621 and Houben-Weyl, Methoden der organischen Chemie, Schwefel-, Selen-, Tellur-Verbindungen, Georg Thieme Verlag Stuttgart 1955, pages 304-309) and subsequently alkylated to give the methyl sulfone as described for example in Houben-Weyl, Methoden der organischen Chemie 4th edition, Organo-Schwefel-Verbindungen, part 2, Georg Thieme Verlag Stuttgart 1985, pages 1145-1149. Simultaneous esterification of the carboxylic acid to the methyl ester takes place.

Compounds of formula I in which R1 is hydrogen are prepared by carrying out the synthesis without steps b and c.

Compounds of formula I in which R3 is NR9R10 are prepared by carrying out the synthesis without step i.

Functional groups in the starting compounds may also be present in protected form or in the form of precursors, and then be converted into the desired groups in the compounds of formula II prepared by the process described above.

Corresponding protective group techniques are known to those skilled in the art.

It is likewise possible for appropriate functional groups to be derivatized by methods known to the skilled worker. For example, compounds in which R3 is $NH_2$ can be converted by reaction with appropriate alkyl halides or 2,2,2-trifluoroethyl halides, for example methyl iodide, ethyl iodide or 2,2,2-trifluoroethyl iodide, into compounds in which R3 is NR9R10, where R9 and R10 are, independently of one another, hydrogen, alkyl having 1, 2, 3 or 4 carbon atoms or —$CH_2$—$CF_3$ and are not both simultaneously hydrogen.

Pentafluorosulfanylbenzoylguanidines of formula I are generally weak bases and are able to bind acids to form salts. Suitable acid addition salts are salts of all pharmaceutically acceptable acids, for example halides, in particular hydrochlorides, lactates, sulfates, citrates, tartrates, acetates, phosphates, methylsulfonates, p-toluenesulfonates.

The compounds of formula I are substituted acylguanidines and inhibit the cellular sodium-proton antiporter ($Na^+/H^+$ exchanger, NHE), in particular the subtype NHE-1.

Because of the NHE-inhibitory properties, the compounds of formula I and/or the pharmaceutically acceptable salts thereof are suitable for the prevention and treatment of diseases caused by activation of or caused by an activated NHE, and of diseases caused secondarily by the NHE-related damage.

The compounds of formula I may also be used for treating and preventing diseases by the NHE being only partially inhibited, for example by use of a low dosage.

Since NHE inhibitors predominantly act via their effect on cellular pH regulation, they can generally be combined beneficially with other compounds which regulate the intracellular pH, with suitable combination partners being inhibitors of the carbonic anhydrase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of formula I and/or the pharmaceutically acceptable salts thereof used according to the invention can, because of inhibition of the cellular $Na^+/H^+$ exchange mechanism, be used as medicaments for the treatment of all acute or chronic ischemia-induced damage or diseases induced primarily or secondarily thereby.

This also relates to their use as medicaments for surgical interventions. Thus, the compounds of the present invention can be used during organ transplantations, it being possible to use the compounds both to protect the organs in the donor before and during the removal, to protect removed organs for example during treatment with or storage thereof in physiological bath liquids, and during transference to the recipient organism.

The compounds of the invention are likewise valuable medicaments with a protective effect when performing angioplastic surgical interventions, for example on the heart as well as on peripheral organs and vessels.

The compounds of the invention may also be used when performing bypass operations, for example bypass operations on coronary vessels and in Coronary Artery Bypass Graft (CABG).

Depending on their activity with regard to ischemia-induced damage, the compounds of the invention I may similarly be used in resuscitation after a cardiac arrest.

The compounds of the invention are of interest for medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of formula I and/or the pharmaceutically acceptable salts thereof can be used when there is heart-damaging overproduction of thyroid hormones, thyrotoxicosis, or on external supply of thyroid hormones. The compounds of formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable for example for the treatment of stroke or of cerebral edema.

The compounds of formula I and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonic anhydrase inhibitors, for example with acetazolamide, and with other inhibitors of NHE or of the sodium-dependent chloride-bicarbonate exchanger (NCBE).

The compounds used according to the invention and/or the pharmaceutically acceptable salts thereof are additionally likewise suitable for the treatment of types of shock such as, for example, of allergic, cardiogenic, hypovolemic and bacterial shock.

The compounds of formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydrase such as, for example, with acetazolamide, is particularly beneficial.

NHE1 inhibitors are additionally distinguished by a strong inhibitory effect on the proliferation of cells, for example fibroblast proliferation and the proliferation of smooth vascular muscle cells. The compounds of formula I and/or the pharmaceutically acceptable salts thereof are therefore suitable as valuable therapeutic agents for diseases in which proliferation represents a primary or secondary cause, and can therefore be used as antiatherosclerotics, agents for chronic renal failure, cancers.

It was possible to show that cell migration is inhibited by NHE inhibitors. The compounds of formula I and/or the pharmaceutically acceptable salts thereof are therefore suitable as valuable therapeutic agents for diseases in which cell migration represents a primary or secondary cause, such as, for example, cancers with a pronounced tendency to metastasis.

NHE1 inhibitors are further distinguished by a retardation or prevention of fibrotic disorders. Compounds of formula I and/or the pharmaceutically acceptable salts thereof are thus suitable as agents for the treatment of cardiac fibroses, and of pulmonary fibrosis, hepatic fibrosis, renal fibrosis and other fibrotic disorders. They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of formula I and/or the pharmaceutically acceptable salts thereof are suitable for the prevention and treatment of high blood pressure and for the treatment of cardiovascular disorders. In these cases they can be used alone or with a suitable combination and formulation partner for the treatment of high blood pressure and of cardiovascular disorders. Thus, for example, one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, can be combined. The NHE inhibitors of the present invention can further be used in combination with calcium channel blockers such as verapanil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. The compounds of the invention can additionally be employed for the prevention or treatment of disorders caused by protozoa, such as malaria and coccidiosis in poultry.

It has additionally been found that NHE1 inhibitors show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the NHE1 inhibitors lead to a marked reduction in the infarctions induced by metabolic abnormalities and, in particular, to a significant reduction in the induced infarct size and the severity thereof.

The compounds of formula I and/or the pharmaceutically acceptable salts thereof are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists.

A combination of an NHE inhibitor of formula I and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of formula I and/or the pharmaceutically acceptable salts thereof, proves to be a favorable combination with enhanced effect and reduced use of active ingredients.

Thus, compounds of formula I and/or the pharmaceutically acceptable salts thereof lead to effective protection against endothelial damage of various origins. This protection of the vessels against the syndrome of endothelial dysfunction means that the compounds of formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that NHE1 inhibitors are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizor or with meglitinide.

Besides the acute antidiabetic effects, the compounds of formula I and/or the pharmaceutically acceptable salts thereof counteract the development of late complications of diabetes and can therefore be used as medicaments for the prevention and treatment of late damage from diabetes, such as diabetic nephropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

NHE1 inhibitors show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors.

The compounds of formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart that is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of formula I and/or the pharmaceutically acceptable salts thereof are thus outstandingly suitable for the treatment and prevention of heart failure, of congestive heart failure (CHF).

Not only is it possible to cure a cancer that has already occurred through inhibition of proliferation, but there is also reduction and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of formula I and/or the pharmaceutically acceptable salts thereof are thus suitable for the treatment and, in particular, the prevention of age-related types of cancer.

With NHE inhibitors, a delay, shifted highly significantly in time is found in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{+2}$ antagonists etc. or with metabolism-normalizing medicaments such as cholesterol-lowering agents.

The compounds of formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds used according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

Also claimed is a medicine for human, veterinary or phytoprotective use, comprising an effective amount of a compound of formula I and/or the pharmaceutically acceptable salts thereof, together with pharmaceutically acceptable carriers and additives, alone or in combination with other active pharmaceutical ingredients or medicaments.

Medicaments which comprise a compound of formula I and/or the pharmaceutically acceptable salts thereof can in this connection be administered, for example, orally, parenterally, intravenously, rectally, transdermally or by inhalation, the preferred administration being dependent on the particular characteristics of the disorder. The compounds of formula I may moreover be used alone or together with pharmaceutical excipients, both in veterinary medicine and in human medicine. The medicaments generally comprise active ingredients of formula I and/or the pharmaceutically acceptable salts thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers that can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g., ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of formula I and/or the pharmaceutically acceptable salts thereof in a pharmaceutically acceptable solvent such as, in particular, ethanol or water, or a mixture of such solvents. Formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of formula I and/or the pharmaceutically acceptable salts thereof for a patient weighing about 75 kg is at least 0.001 mg/kg, preferably 0.01 mg/kg, to a maximum of 10 mg/kg, preferably 1 mg/kg, of body weight. For acute episodes of the disorder, for example immediately after suffering a myocardial infarction, higher and, in particular, more frequent dosages may also be necessary, e.g., up to 4 single doses a day. Up to 700 mg a day may be necessary, in particular on i.v. administration, for example for a patient with infarction in the intensive care unit, and the compounds of the invention can be administered by infusion.

LIST OF ABBREVIATIONS

ADMET absorption—distribution—metabolism—excretion—toxicology
CDI diimidazol-1-ylmethanone
dba dibenzylideneacetone
DIP diisopropyl ether
DIPEA diisopropylethylamine
DME 1,2-dimethoxyethane
DMF N,N-dimethylformamide
DMSO dimethyl sulfoxide
EA ethyl acetate
eq. equivalent
HOAc acetic acid
KOtBu potassium 2-methylpropan-2-olate
MeOH methanol
mp melting point
MTB tert-butyl methyl ether
NMP N-methyl-2-pyrrolidone
OAc acetate
dppf 1,1'-bis(diphenylphosphino)ferrocene
RT room temperature
TBF tetrahydrofuran
TMEDA N,N,N',N'-tetramethylethane-1,2-diamine

EXAMPLES

Example 1

N-(5-Methanesulfonyl-2-methyl-4-pentafluorosulfanylbenzoyl)guanidine

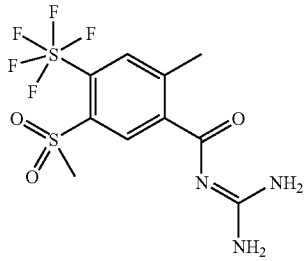

a) 4-Aminophenylsulfur pentafluoride

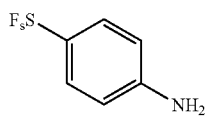

A solution of tin(II) chloride (1465 g, 7.73 mol) in concentrated (32 percent) aqueous HCl solution was heated with stirring to 80° C. and then, with ice cooling, 4-nitrophenylsulfur pentafluoride (584 g, 2.344 mol) was introduced in 8 portions over the course of 1 h. The internal temperature was kept below 100° C. during this. Subsequently, the mixture was stirred at an internal temperature of 85° C. for 1.5 h and then cooled to 45° C. over the course of a further hour. A mixture of ice (12 kg), NaOH (2 kg) and dichloromethane (1.5 l) was prepared and the reaction mixture was added with vigorous stirring. The phases were separated, the aqueous phase was extracted 3 times with 1 l of dichloromethane each time, and the combined organic phases were dried over $Na_2SO_4$ and evaporated in vacuo. 510 g of 4-aminophenylsulfur pentafluoride were obtained as a pale yellow crystalline powder, m.p. 63-65° C.

b) 4-Amino-3-bromophenylsulfur pentafluoride

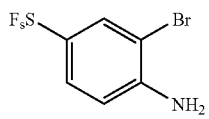

4-Aminophenylsulfur pentafluoride (510 g, 2.327 mol) was dissolved in dichloromethane (7 l), the solution was cooled to 5° C. and, while stirring, 1,3-dibromo-5,5-dimethylimidazolidine-2,4-dione (326 g, 1.14 mol) was introduced in several portions with ice cooling so that the internal temperature was kept at 3-8° C. (approx. 1 h). The mixture was then left to stir and warm to room temperature without external cooling for 1 h. The mixture was filtered through a bed of silica gel (volume about 1 l) and washed with dichloromethane (5.5 l), and the filtrate was evaporated in vacuo. About 700 g of a red-brown crystalline mass was obtained and was dissolved in n-heptane (600 ml) at 60° C. and then crystallized in a refrigerator at 4° C. Filtration with suction resulted in 590 g (85%) of 4-amino-3-bromophenylsulfur pentafluoride as brownish crystals, m.p. 59-59.5° C.

c) 4-Amino-3-methylphenylsulfur pentafluoride

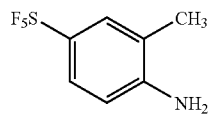

A mixture of $Cs_2CO_3$ (794 g, 2.7 mol), dimethoxyethane (2 l), water (300 ml) and trimethylboroxine (50 percent solution in THF, 225 g, 0.9 mol) was heated to 70° C., $PdCl_2$ (dppf)× $CH_2Cl_2$ (37 g, 45 mmol) was added, and a solution of 4-amino-3-bromophenylsulfur pentafluoride (270 g, 0.9 mol) in dimethoxyethane (400 ml) was added dropwise over the course of 2 h while the reaction mixture was heated to reflux. It was subsequently heated under reflux for a further 3 h and then cooled to room temperature, diluted with MTB ether (500 ml), filtered through a silica gel column (14×7 cm, 70-200 μm) and washed with MTB ether (2500 ml). The filtrate was evaporated in vacuo. 490 g of a black, semicrystalline mass was obtained and was subjected to a steam distillation. A total of 5.5 l of condensate was collected, from which the crystals of the product separated out. The condensate was extracted 3× with MTB ether, and the combined organic phases were dried over $Na_2SO_4$ and evaporated in vacuo. 4-Amino-3-methylphenylsulfur pentafluoride (181 g, 76%) was obtained as colorless crystals, m.p. 65-66° C., d) 4-Bromo-3-methylphenylsulfur pentafluoride

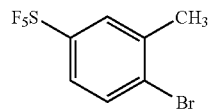

A mixture of tert-butyl nitrite (90 percent pure, 37 ml, 280 mmol) and $CuBr_2$ (35.8 g, 160 mmol) in acetonitrile (260 ml) was cooled to 5° C. and, while stirring and cooling with ice, a solution of 4-amino-3-methylphenylsulfur pentafluoride (30.9 g, 132.5 mmol) in MTB ether (140 ml) was added dropwise at 5-8° C. over the course of 1 h. Evolution of nitrogen started after about 2 min. The mixture was then allowed to warm with stirring to room temperature over the course of 1 h, a mixture of ice (250 g), 26 percent aqueous $NH_3$ solution (50 ml) and MTB ether (250 ml) was added, and the mixture was stirred for 10 min. The phases were separated, the aqueous was extracted 3× with MTB ether (150 ml each time), and the combined organic phases were shaken once with 400 ml of water. Drying with $Na_2SO_4$ and evaporation of the organic phase resulted in 39 g of 4-bromo-3-methylphenylsulfur pentafluoride as a red-brown oil which was contaminated with 8 mol % of 4,5-dibromo-3-methylphenylsulfur pentafluoride, but was used further without further purification. Yield 89% based on a purity of 90%.

e) 4-Cyano-3-methylphenylsulfur pentafluoride

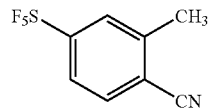

A mixture of 4-bromo-3-methylphenylsulfur pentafluoride (136.4 g, purity 80%, 0.367 mol), Zn(CN)$_2$ (72.8 g, 0.62 mol) and Zn dust (7.2 g, 0.11 mol) in dimethylacetamide (900 ml) and water (40 ml) was heated with stirring and nitrogen blanketing to 125° C., and PdCl$_2$(dppf)×CH$_2$Cl$_2$ (32.7 g, 40 mmol) was added. After stirring at 125° C. for one hour, PdCl$_2$(dppf)×CH$_2$Cl$_2$ (16.3 g, 20 mmol) and Zn dust (3.6 g, 55 mmol) were again added, and stirring was continued at 125° C. for 2 h. The mixture was then cooled to room temperature, diluted with n-heptane (400 ml) and stirred vigorously with addition of 5 N aqueous NH$_4$Cl solution (250 ml) and water (450 ml) for 15 min. The mixture was filtered with suction through a layer of kieselguhr, the phases were separated, and the aqueous was extracted 2× with n-heptane (200 ml). The combined organic phases were shaken with water (450 ml), dried over MgSO$_4$ and evaporated in vacuo. The resulting black residue was dissolved in 200 ml of n-heptane, filtered and again evaporated in vacu 78 g of a dark brown liquid were obtained and were purified by chromatography on a silica gel column (7×55 cm, 60-200 μm, n-heptane/dichloromethane 4:1 to 3:2). The first fraction obtained was 6.5 g of 4-bromo-3-methylphenylsulfur pentafluoride (precursor) as yellowish liquid, and then 71.1 g (80%) of 4-cyano-3-methylphenylsulfur pentafluoride as pale yellow oil.

f) 2-Methyl-4-pentafluorosulfanylbenzoic acid

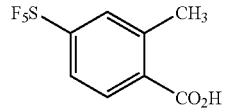

A mixture of 4-cyano-3-methylphenylsulfur pentafluoride (41.2 g, 169.4 mmol), NaOH (20.4 g, 510 mmol) and water (60 ml) in ethylene glycol (160 ml) was heated to 130° C. and stirred at this temperature for 4 h. It was then cooled to room temperature and diluted with MTB ether (150 ml) and water (250 ml), and the mixture was filtered with suction. The phases of the filtrate were separated, and the aqueous was acidified with concentrated aqueous HCl solution, and the precipitated solid was filtered off with suction. 41.1 g (93%) of 2-methyl-4-pentafluorosulfanylbenzoic acid were obtained as colorless crystals, m.p. 138-139° C.

g) 2-Methyl-5-nitro-4-pentafluorosulfanylbenzoic acid

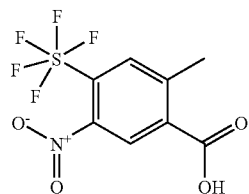

6.0 g of 2-methyl-4-pentafluorosulfanylbenzoic acid were dissolved in 60 ml of a 90% aqueous HNO$_3$ solution and, at RT, 6 ml of a 96% H$_2$SO$_4$ were added dropwise. The mixture was left to stand at RT for 28 h and then poured into 300 g of ice, 300 ml of water were added and, after stirring for 1 h, the product was filtered off. Drying in air resulted in 6.5 g of a pale yellow solid, mp. 218-220° C.

R$_f$(DIP/2% HOAc)=0.27 MS (ES$^-$): 306 h) 5-Amino-2-methyl-4-pentafluorosulfanylbenzoic acid

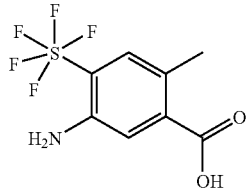

6.5 g of 2-methyl-5-nitro-4-pentafluorosulfanylbenzoic acid were dissolved in 100 ml of MeOH and 20 ml of HOAc, and 500 mg of 10% Pd/C were added. Hydrogenation was carried out under hydrogen at atmospheric pressure and RT for 20 h. The reaction was incomplete and therefore hydrogenation was continued under a pressure of 6 bar of hydrogen and at RT for 48 h. The catalyst was then filtered off and the solvents were removed in vacuo. 5.7 g of a pale grey solid were obtained, mp. 187-189° C.

R$_f$(DIP/2% HOAc)=0.23 MS (ES$^-$): 276 i) 5-Chlorosulfonyl-2-methyl-4-pentafluorosulfanylbenzoic acid

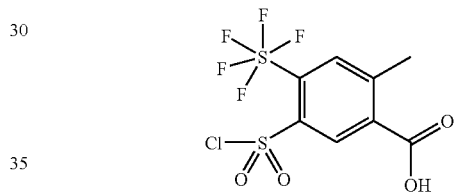

1.0 g of 5-amino-2-methyl-4-pentafluorosulfanylbenzoic acid was dissolved in 30 ml of HOAc, and 30 g of ice and 30 ml of a saturated aqueous HCl solution were added. Then, at 0° C., a solution of 274 mg of NaNO$_2$ in 1 ml of water was added dropwise over the course of one minute. The mixture was stirred at 0° C. for 15 minutes. The resulting suspension was then added in portions to a suspension, cooled to 0° C., of 6.1 mg of CuCl and 61.5 mg of CuCl$_2$×2H$_2$O in 30 ml of a saturated solution of SO$_2$ in HOAc. The mixture was stirred at 0° C. for 1 h and then at RT for 1 h. The reaction mixture was subsequently extracted 3 times with 200 ml of diethyl ether each time. MgSO$_4$ was used for drying, and the volatile constituents were removed in vacuo. 1.3 g of the product were obtained and immediately reacted further.

k) 2-Methyl-5-sulfino-4-pentafluorosulfanylbenzoic acid

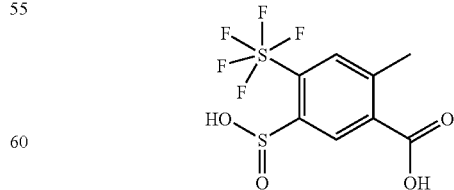

1.2 g of 5-chlorosulfonyl-2-methyl-4-pentafluorosulfanyl-benzoic acid were added in portions to a solution, heated to 70° C., of 4.2 g of Na$_2$SO$_3$ in 50 ml of water and, during this, the pH of the solution was kept between pH=9 and pH=11 with a 2N aqueous NaOH solution. The mixture was stirred at 70° C. for 20 minutes, cooled to RT and adjusted to pH=1-2 with an aqueous HCl solution. The mixture was left to stand at RT for 16 h and then the product was filtered off and dried in vacuo. 1.0 g of a white solid was obtained, mp. 288-290° C. (with decomposition).

$R_f$(EA/MeOH 1:1)=0.52 l) Methyl 5-methanesulfonyl-2-methyl-4-pentafluorosulfanylbenzoate

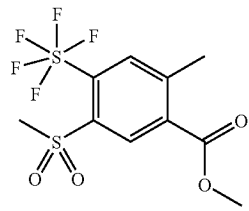

1.0 g of 2-methyl-5-sulfino-4-pentafluorosulfanylbenzoic acid was suspended in 10 ml of water, and 3.1 ml of an aqueous 2N NaOH solution were added (phenolphthalein: basic). The water was removed in vacuo and then coevaporated twice with 20 ml of toluene each time. The disodium salt was then dissolved in 40 ml of anhydrous DMF and, after addition of 0.69 ml of methyl iodide, stirred initially at 60° C. for 4 h and then at RT for 15 h. The reaction mixture was poured into 100 ml of water and a first portion of the product (500 mg) was filtered off with suction. The filtrate was adjusted to pH=2 with aqueous HCl solution and extracted 3 times with 30 ml of EA each time. MgSO₄ was used for drying, and the solvent was removed in vacuo. Chromatography on silica gel with DIP afforded a further 460 mg of white crystals, mp 127° C.

$R_f$(DIP)=0.36 m) N-(5-Methanesulfonyl-2-methyl-4-pentafluorosulfanylbenzoyl)guanidine 0.70 g of guanidine chloride and 0.68 g of KOtBu were stirred in 20 ml of anhydrous DMF at RT for 30 minutes. This suspension was then added to 0.43 g of methyl 5-methanesulfonyl-2-methyl-4-pentafluorosulfanylbenzoate and stirred at RT for 16 h. The reaction mixture was then poured into 200 ml of water, adjusted to pH=8 with aqueous HCl solution and extracted 3 times with 100 ml of EA each time. MgSO₄ was used for drying, and the solvent was removed in vacuo. The residue was suspended in 5 ml of CH₂Cl₂ and the product was filtered off. 190 mg of colorless crystals were obtained, mp. 254-256° C.

$R_f$(EA)=0.22 MS (ES⁺): 382

Example 2

N-(5-Methanesulfonyl-2-methyl-4-pentafluorosulfanylbenzoyl)-guanidine methanesulfonic acid salt

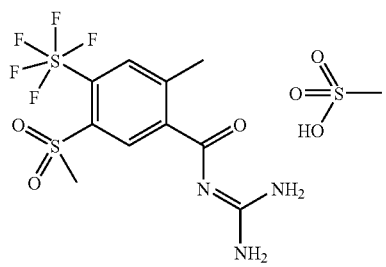

9.3 g of the title compound of example 1 were suspended in 100 ml of water and a solution of 2.3 g of methanesulfonic acid in 10 ml of water was added. The mixture was subsequently stirred at RT for 30 minutes and then the water was removed under reduced pressure to obtain 11.7 g of the methanesulfonic acid salt, which was subsequently recrystallized from 110 ml of water to obtain 10.0 g of N-(5-methanesulfonyl-2-methyl-4-pentafluorosulfanylbenzoyl)guanidine methanesulfonic acid salt as white crystals, m.p. 230° C.

Example 3

N-(5-Methanesulfonyl-2-methyl-4-pentafluorosulfanylbenzoyl)-guanidine hydrochloride

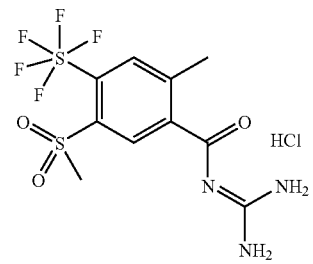

300 mg of the title compound of example 2 were suspended in 50 ml of a saturated aqueous Na₂CO₃ solution and extracted twice with 40 ml of EA each time. The EA phase was subsequently dried over MgSO₄ and the solvent was removed under reduced pressure. The residue was dissolved in 10 ml of MeOH and admixed with 2 ml of a 10% aqueous HCl solution. The volatiles were removed under reduced pressure to leave 230 mg of white crystals, m.p. 276-278° C.

Determination of the NHE Inhibition

The inhibitory concentration $IC_{50}$ for NHE-1 inhibition was determined as follows:

$IC_{50}$ for NHE-1 inhibition was determined in an FLIPR assay by measurement of the $pH_i$ recovery in transfected cell lines which express human NHE-1.

The assay was carried out in an FLIPR (fluorometric imaging plate reader) with black-walled 96-well microtiter plates with clear bases. The transfected cell lines expressing the various NHE subtypes (the parental cell line LAP-1 shows no endogenous NHE activity as a result of mutagenesis and subsequent selection) were seeded the preceding day at a density of ~25 000 cells/well.

The growth medium for the transfected cells (Iscove+10% fetal calf serum) additionally contained G418 as selection antibiotic in order to ensure the presence of the transfected sequences.

The actual assay started with the removal of the growth medium and addition of 100 μl of loading buffer per well (5 μM BCECF-AM [2',7'-bis(carboxyethyl)-5-(and -6-)carboxyfluorescein, acetoxymethyl ester] in 20 mM NH₄Cl, 115 mM choline chloride, 1 mM MgCl₂, 1 mM CaCl₂, 5 mM KCl, 20 mM HEPES, 5 mM glucose; pH 7.4 [adjusted with KOH]). The cells were then incubated at 37° C. for 20 minutes. This incubation led to loading of the cells with the fluorescent dye whose fluorescence intensity depends on $pH_i$, and with NH₄Cl that made the cells slightly alkaline.

The nonfluorescent dye precursor BCECF-AM is, as ester, membrane-permeable. The actual dye BCECF is not membrane-permeable but is liberated inside cells by esterases.

After this incubation for 20 minutes, the loading buffer which contained NH₄Cl and free BCECF-AM was removed by washing three times in a cell washer (Tecan Columbus) with in each case 400 μl of washing buffer (133.8 mM choline chloride, 4.7 mM KCl, 1.25 mM MgCl₂, 1.25 mM CaCl₂, 0.97 mM K₂HPO₄, 0.23 mM KH₂PO₄, 5 mM HEPES, 5 mM glucose; pH 7.4 [adjusted with KOH]). The residual volume which remained in the wells was 90 μl (50-125 μl possible). This washing step removed the free BCECF-AM and results, as a consequence of the removal of the external $NH_4^+$ ions, in intracellular acidification (~$pH_i$ 6.3-6.4).

Since the equilibrium of intracellular $NH_4^+$ with $NH_3$ and $H^+$ was disturbed by the removal of the extracellular $NH_4^+$ and by the subsequent instantaneous passage of the $NH_3$ through the cell membrane, the washing process resulted in $H^+$ remaining inside the cells, which was the cause of the intracellular acidification. This may eventually lead to cell death if it persists long enough.

It was important at this point that the washing buffer was sodium-free (<1 mM) because extracellular sodium ions would lead to an instantaneous recovery of the $pH_i$ through the activity of the cloned NHE isoforms.

It was likewise important for all the buffers used (loading buffer, washing buffer, recovery buffer) not to contain any $HCO_3^-$ ions, because the presence of bicarbonate would lead to activation of interfering bicarbonate-dependent $pH_i$ regulatory systems present in the parental LAP-1 cell line.

The microtiter plates with the acidified cells were then (up to 20 minutes after the acidification) transferred to the FLIPR. In the FLIPR, the intracellular fluorescent dye was excited by light with a wavelength of 488 nm generated by an argon laser, and the measured parameters (laser power, illumination time and aperture of the CCD camera incorporated in the FLIPR) were chosen so that the average fluorescence signal per well is between 30 000 and 35 000 relative fluorescence units.

The actual measurement in the FLIPR started with a photograph being taken by the CCD camera every two seconds under software control. After ten seconds, the recovery of the intracellular pH was initiated by adding 90 μl of recovery buffer (133.8 mM NaCl, 4.7 mM KCl, 1.25 mM MgCl₂, 1.25 mM CaCl₂, 0.97 mM K₂HPO₄, 0.23 mM KH₂PO₄, 10 mM HEPES, 5 mM glucose; pH 7.4 [adjusted with NaOH]) by means of the 96-well pipettor incorporated in the FLIPR.

Positive control wells (100% NHE activity) were those to which pure recovery buffer is added, while negative controls (0% NHE activity) received washing buffer. Recovery buffer with twice the concentration of test substance was added to all the other wells. Measurement in the FLIPR terminated after 60 measurements (two minutes).

The raw data are exported into the ActivityBase program. This program firstly calculates the NHE activities for each tested substance concentration and, from these, the $IC_{50}$ values for the substances. Since the progress of $pH_i$ recovery was not linear throughout the experiment, but fell at the end owing to decreasing NHE activity at higher $pH_i$ values, it was important to select for evaluation of the measurement the part in which the increase in fluorescence of the positive controls was linear.

| Example | NHE1 inhibition $IC_{50}$ [nM] |
|---|---|
| 1 | 49 |

In vivo pharmacokinetics—profiling with the "n in one method"

The exposure data and the volumes of distribution were determined as characteristic pharmacokinetic data as follows:

The NHE-1 inhibitor of example 1 of the invention and, as reference substance, the known NHE-1 inhibitor cariporide with formula

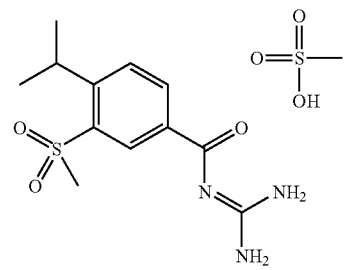

were dissolved in an aqueous, slightly acidic medium (water, pH 4, adjusted with 1M hydrochloric acid). The concentration of the aqueous formulation prepared in this way was about 1.5 mg of each substance per 1 g of solution. 10 ml of this formulation were administered as a single bolus by catheter into the jugular vein of a fasting male beagle dog (dose about 1 mg of each substance administered per kg of the dog's body weight). Blood samples were taken by means of a second catheter after 5 min, 15 min, 30 min, 1 h, 2 h, 4 h, 8 h and 24 h, and heparinized plasma was prepared by centrifugation at 1000 G in appropriate plasma tubes.

The plasma samples were worked up and, after an HPLC separation, quantified by MS/MS. The high specificity of this method permitted simultaneous determination of a plurality of substances. The exposures could be calculated using the WinNonlin computer program from the concentration-time plots (see FIG. 1) and compared with the exposure of the known NHE-1 reference substance. Since the various substances were measured in the same animal at the same time, the result was an accurate comparison of the compounds, and a ranking of the volumes of distribution was possible.

| Compound | Volume of distribution [l/kg of body weight] |
|---|---|
| Example 1 | 1.67 |
| Reference substance cariporide | 2.94 |

It is evident from the concentration-time plots in FIG. 1 that the compound of the invention is retained in the blood also over a longer period and thus the exposure is about 2-3 times higher than with the reference substance cariporide. Cariporide is no longer detectable in the plasma after 24 hours.

The captions and signs in the FIGURE were as follows:

FIG. 1: concentration-time plots in the blood plasma of dogs after administration of in each case approx. 1 mg/kg of the compound of example 1 and of cariporide.

y axis: concentration of the measured compound in the μg/ml in plasma x axis: time in h

I claim:
1. A compound of formula I

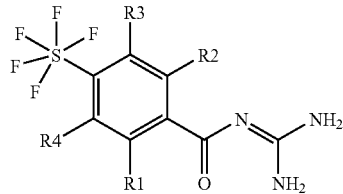

wherein R1 is hydrogen, alkyl having 1, 2, 3 or 4 carbon atoms, alkoxy having 1, 2, 3 or 4 carbon atoms, F, Cl, Br, I, —CN, NR5R6, —O$_p$—(CH$_2$)$_n$—(CF$_2$)$_o$—CF$_3$ or —(SO$_m$)$_q$—(CH$_2$)$_r$—(CF$_2$)$_s$—CF$_3$;

R5 and R6 are, independently of one another, hydrogen, alkyl having 1, 2, 3 or 4 carbon atoms or —CH$_2$—CF$_3$;

m is zero, 1 or 2;

n, o, p, q, r and s are, independently of one another, zero or 1;

R2 is hydrogen, alkyl having 1, 2, 3 or 4 carbon atoms, alkoxy having 1, 2, 3 or 4 carbon atoms, F, Cl, Br, I, —CN, NR7R8, —O$_t$—(CH$_2$)$_u$—(CF$_2$)$_v$—CF$_3$ or —(SO$_w$)$_x$—(CH$_2$)$_y$—(CF$_2$)$_z$—CF$_3$;

R7 and R8 are, independently of one another, hydrogen, alkyl having 1, 2, 3 or 4 carbon atoms, or —CH$_2$—CF$_3$;

w is zero, 1 or 2;

t, u, v, x, y and z are, independently of one another, zero or 1;

R3 is Cl, Br, I, —CN, —SO$_2$CH$_3$, alkoxy having 1, 2, 3 or 4 carbon atoms, NR9R10, —O$_a$—(CH$_2$)$_b$—(CF$_2$)$_c$—CF$_3$, —(SO$_d$)$_e$—(CH$_2$)$_f$—(CF$_2$)$_g$—CF$_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be replaced by fluorine atoms;

R9 and R10 are, independently of one another, hydrogen, alkyl having 1, 2, 3 or 4 carbon atoms, or —CH$_2$—CF$_3$;

a, b and c are, independently of one another, zero or 1;

d is zero, 1 or 2;

e is zero or 1;

f is zero, 1, 2, 3 or 4;

g is zero or 1;

or R3 is —(CH$_2$)$_h$-phenyl or —O-phenyl, in which the phenyl radicals are unsubstituted or substituted by 1, 2 or 3 radicals selected from the group consisting of F, Cl, Br, I, —O$_j$—(CH$_2$)$_k$—CF$_3$, alkoxy having 1, 2, 3 or 4 carbon atoms, alkyl having 1, 2, 3 or 4 carbon atoms, and —SO$_2$CH$_3$;

j is zero or 1;

k is zero, 1, 2 or 3;

h is zero, 1, 2, 3 or 4;

or R3 is —(CH$_2$)$_{aa}$-heteroaryl, which is unsubstituted or substituted by 1, 2 or 3 radicals selected from the group consisting of F, Cl, Br, I, —O$_{bb}$—(CH$_2$)$_{cc}$—CF$_3$, alkoxy having 1, 2, 3 or 4 carbon atoms, alkyl having 1, 2, 3 or 4 carbon atoms, and —SO$_2$CH$_3$;

bb is zero or 1;

cc is zero or 1, 2 or 3;

aa is zero, 1, 2, 3 or 4;

R4 is hydrogen, F, Cl, Br, I, —CN, —SO$_2$CH$_3$, alkoxy having 1, 2, 3 or 4 carbon atoms, NR11R12, —O$_{dd}$—(CH$_2$)$_{ee}$—(CF$_2$)$_{ff}$—CF$_3$; —(SO$_{gg}$)$_{hh}$—(CH$_2$)$_{jj}$—(CF$_2$)$_{kk}$—CF$_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be substituted by fluorine atoms;

R11 and R12 are, independently of one another, hydrogen, alkyl having 1, 2, 3 or 4 carbon atoms or —CH2—CF3;

dd, ee and ff are, independently of one another, zero or 1;

gg is zero, 1 or 2;

hh is zero or 1;

jj is zero, 1, 2, 3 or 4;

kk is zero or 1;

or R4 is —(CH$_2$)$_{ll}$-phenyl or —O-phenyl, wherein the phenyl radicals are unsubstituted or substituted by 1, 2 or 3 radicals selected from the group consisting of F, Cl, Br, I, —O$_{mm}$—(CH$_2$)$_{nn}$—CF$_3$, alkoxy having 1, 2, 3 or 4 carbon atoms, alkyl having 1, 2, 3 or 4 carbon atoms, and —SO$_2$CH$_3$;

mm is zero or 1;

nn is zero, 1, 2 or 3;

ll is zero, 1, 2, 3 or 4;

or R4 is —(CH$_2$)$_{oo}$-heteroaryl, which is unsubstituted or substituted by 1, 2 or 3 radicals selected from the group consisting of F, Cl, Br, I, —O$_{pp}$—(CH$_2$)$_{rr}$—CF$_3$, alkoxy having 1, 2, 3 or 4 carbon atoms, alkyl having 1, 2, 3 or 4 carbon atoms, and —SO$_2$CH$_3$;

pp is zero or 1;

rr is zero, 1, 2 or 3; and oo is zero, 1, 2, 3 or 4, and the pharmaceutically acceptable salts thereof.

2. The compound of claim 1 wherein R1 is hydrogen, alkyl having 1, 2, 3 or 4 carbon atoms, alkoxy having 1, 2, 3 or 4 carbon atoms, F, Cl, Br, I, —CN, NR5R6, —O$_{p-(CH2)_n}$—(CF$_2$)$_o$—CF$_3$ or —(SO$_m$)$_q$—(CH$_2$)$_r$—(CF$_2$)$_s$—CF$_3$;

R5 and R6 are, independently of one another, hydrogen, alkyl having 1, 2, 3 or 4 carbon atoms, or —CH$_2$—CF$_3$;

m is zero, 1 or 2;

n, o, p, q, r and s are, independently of one another, zero or 1;

R2 is hydrogen or F;

R3 is Cl, Br, I, —CN, —SO$_2$CH$_3$, alkoxy having 1, 2, 3 or 4 carbon atoms, NR9R10, —O$_a$—(CH$_2$)$_b$—(CF$_2$)$_c$—CF$_3$, —(SO$_d$)$_e$—(CH$_2$)$_f$—(CF$_2$)$_g$—CF$_3$, alkyl having 1, 2, 3, 4, 5 or 6 carbon atoms, or cycloalkyl having 3, 4, 5, 6, 7 or 8 carbon atoms, wherein 1, 2, 3 or 4 hydrogen atoms may be replaced by fluorine atoms;

R9 and R10 are, independently of one another, hydrogen, alkyl having 1, 2, 3 or 4 carbon atoms, or —CH$_2$—CF$_3$;

a, b and c are, independently of one another, zero or 1;

d is zero, 1 or 2;

e is zero or 1;

f is zero, 1, 2, 3 or 4;

g is zero or 1;

or R3 —(CH$_2$)$_h$-phenyl or —O-phenyl, wherein the phenyl radicals are unsubstituted or substituted by 1, 2 or 3 radicals selected from the group consisting of F, Cl, Br, I, —O$_j$—(CH$_2$)$_k$—CF$_3$, alkoxy having 1, 2, 3 or 4 carbon atoms, alkyl having 1, 2, 3 or 4 carbon atoms, and —SO$_2$CH$_3$;

j is zero or 1;

k is zero, 1, 2 or 3;

h is zero, 1, 2, 3 or 4;

or R3 is —(CH$_2$)$_{aa}$-heteroaryl, which is unsubstituted or substituted by 1, 2 or 3 radicals selected from the group consisting of F, Cl, Br, I, —O$_{bb}$—(CH$_2$)$_{cc}$—CF$_3$, alkoxy having 1, 2, 3 or 4 carbon atoms, alkyl having 1, 2, 3 or 4 carbon atoms, and —SO$_2$CH$_3$;

bb is zero or 1;

cc is zero, 1, 2 or 3;

aa zero, 1, 2, 3 or 4; and

R4 is hydrogen or F, and the pharmaceutically acceptable salts thereof.

3. The compound of claim 1 wherein R1 is hydrogen, alkyl having 1, 2, 3 or 4 carbon atoms, alkoxy having 1, 2, 3 or 4 carbon atoms, F, Cl, Br, I, —CN, NR5R6, —O—CH$_2$—CF$_3$, or —(SO$_m$)$_q$—(CH$_2$)$_r$—CF$_3$;

R$_5$ and R$_6$ are, independently of one another, hydrogen, alkyl having 1, 2, 3 or 4 carbon atoms, or —CH$_2$—CF$_3$;
m is zero, 1 or 2;
q and r are, independently of one another, zero or 1;
R2 is hydrogen or F;
R3 is Cl, Br, I, —CN, —SO$_2$CH$_3$, alkoxy having 1, 2, 3 or 4 carbon atoms, NR9R10, —O—CH$_2$—CF$_3$, —(SO$_d$)$_e$—CF$_3$, alkyl having 1, 2, 3, 4, 5 or 6 carbon atoms, or cycloalkyl having 3, 4, 5, 6, 7 or 8 carbon atoms, wherein 1, 2, 3 or 4 hydrogen atoms may be replaced by fluorine atoms;
R9 and R10 are, independently of one another, hydrogen, alkyl having 1, 2, 3 or 4 carbon atoms, or —CH$_2$—CF$_3$;
d is zero, 1 or 2;
e is zero or 1;
or R3 is phenyl, which is unsubstituted or substituted by 1, 2 or 3 radicals selected from the group consisting of F, Cl, Br, I, —O$_j$—(CH$_2$)$_k$—CF$_3$, alkoxy having 1, 2, 3 or 4 carbon atoms, alkyl having 1, 2, 3 or 4 carbon atoms, and —SO$_2$CH$_3$;
zero or 1;
k is zero, 1, 2 or 3;
or R3 is heteroaryl, which is unsubstituted or substituted by 1, 2 or 3 radicals selected from the group consisting of F, Cl, Br, I, —O$_{bb}$—(CH$_2$)$_{cc}$—CF$_3$, alkoxy having 1, 2, 3 or 4 carbon atoms, alkyl having 1, 2, 3 or 4 carbon atoms, and —SO$_2$CH$_3$;
bb is zero or 1;
cc is zero, 1, 2 or 3; an
R4 is hydrogen or F, and the pharmaceutically acceptable salts thereof.

4. The compound of claim 1 wherein R1 is hydrogen, alkyl having 1, 2, 3 or 4 carbon atoms, methoxy, ethoxy, F, Cl, NR5R6, —O—CH$_2$—CF$_3$, or —(SO$_m$)$_q$—(CH$_2$)$_r$—CF$_3$;
R5 and R6 are, independently of one another, hydrogen, alkyl having 1, 2, 3 or 4 carbon atoms, or —CH$_2$—CF$_3$;
m is zero, 1 or 2;
q and r are, independently of one another, zero or 1;
R2 is hydrogen or F;
R3 is Cl, —CN, —SO$_2$CH$_3$, methoxy, ethoxy, NR9R10, —O—CH$_2$—CF$_3$, —(SO$_d$)$_e$—CF$_3$, alkyl having 1, 2, 3, 4, 5 or 6 carbon atoms, or cycloalkyl having 3, 4, 5, 6 or 7 carbon atoms, wherein 1, 2, 3 or 4 hydrogen atoms may be replaced by fluorine atoms;
R9 and R10 are, independently of one another, hydrogen, methyl, ethyl or —CH$_2$—CF$_3$;
d is zero, 1 or 2;
e is zero or 1;
or R3 is phenyl, which is unsubstituted or substituted by 1 or 2 radicals selected from the group consisting of F, Cl, —O$_j$—(CH$_2$)$_k$—CF$_3$, methoxy, ethoxy, alkyl having 1, 2, 3 or 4 carbon atoms, and —SO$_2$CH$_3$;
j and k are, independently of one another, zero or 1;
or R3 is heteroaryl, which is unsubstituted or substituted by 1 or 2 radicals selected from the group consisting of F, Cl, —O$_{bb}$—(CH$_2$)$_{cc}$—CF$_3$, methoxy, ethoxy, alkyl having 1, 2, 3 or 4 carbon atoms, and —SO$_2$CH$_3$;
bb and cc are, independently of one another, zero or 1; and
R4 is hydrogen or F, and the pharmaceutically acceptable salts thereof.

5. The compound of claim 1 selected from the group consisting of N-(5-methanesulfonyl-2-methyl-4-pentafluorosulfanylbenzoyl)guanidine, and the pharmaceutically acceptable salts thereof.

6. A process for preparing a compound of formula I

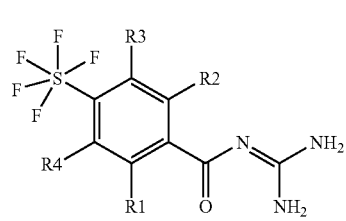

wherein R1 is hydrogen, alkyl having 1, 2, 3 or 4 carbon atoms, alkoxy having 1, 2, 3 or 4 carbon atoms, F, Cl, Br, I, —CN, NR5R6, —O$_p$—(CH$_2$)$_n$—(CF$_2$)$_o$—CF$_3$ or —(SO$_m$)$_q$—(CH$_2$)$_r$(CF$_2$)$_s$—CF$_3$;
R5 and R6 are, independently of one another, hydrogen, alkyl having 1, 2, 3 or 4 carbon atoms or —CH$_2$—CF$_3$;
m is zero, 1 or 2;
n, o, p, q, r and s are, independently of one another, zero or 1;
R2 is hydrogen, alkyl having 1, 2, 3 or 4 carbon atoms, alkoxy having 1, 2, 3 or 4 carbon atoms, F, Cl, Br, I, —CN, NR7R8, —O$_t$—(CH$_2$)$_u$—(CF$_2$)$_v$—CF$_3$ or —(SO$_w$)$_x$—(CH$_2$)$_y$—(CF$_2$)$_z$—CF$_3$;
R7 and R8 are, independently of one another, hydrogen, alkyl having 1, 2, 3 or 4 carbon atoms, or —CH$_2$—CF$_3$;
w is zero, 1 or 2;
t, u, v, x, y and z are, independently of one another, zero or 1;
R3 is Cl, Br, I, —CN, —SO$_2$CH$_3$, alkoxy having 1, 2, 3 or 4 carbon atoms, NR9R10, —O$_a$—(CH$_2$)$_b$—(CF$_2$)$_c$—CF$_3$, —(SO$_d$)$_e$—(CH$_2$)$_f$—(CF$_2$)$_g$—CF$_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be replaced by fluorine atoms;
R9 and R10 are, independently of one another, hydrogen, alkyl having 1, 2, 3 or 4 carbon atoms, or —CH$_2$—CF$_3$;
a, b and c are, independently of one another, zero or 1;
d is zero, 1 or 2;
e is zero or 1;
f is zero, 1, 2, 3 or 4;
g is zero or 1;
or R3 is —(CH$_2$)$_h$-phenyl or —O-phenyl, in which the phenyl radicals are unsubstituted or substituted by 1, 2 or 3 radicals selected from the group consisting of F, Cl, Br, I, —O$_j$—(CH$_2$)$_k$—CF$_3$, alkoxy having 1, 2, 3 or 4 carbon atoms, alkyl having 1, 2, 3 or 4 carbon atoms, and —SO$_2$CH$_3$;
j is zero or 1;
k is zero, 1, 2 or 3;
h is zero, 1, 2, 3 or 4;
or R3 is —(CH$_2$)$_{aa}$-heteroaryl, which is unsubstituted or substituted by 1, 2 or 3 radicals selected from the group consisting of F, Cl, Br, I, —O$_{bb}$—(CH$_2$)$_{cc}$—CF$_3$, alkoxy having 1, 2, 3 or 4 carbon atoms, alkyl having 1, 2, 3 or 4 carbon atoms, and —SO$_2$CH$_3$;
bb is zero or 1;
cc is zero or 1, 2 or 3;
aa is zero, 1, 2, 3 or 4;

R4 is hydrogen, F, Cl, Br, I, —CN, —SO$_2$CH$_3$, alkoxy having 1, 2, 3 or 4 carbon atoms, NR11R12, —O$_{dd}$—(CH$_2$)$_{ee}$—(CF$_2$)$_{ff}$—CF$_3$; —(SO$_{gg}$)$_{hh}$—(CH$_2$)$_{jj}$—(CF$_2$)$_{kk}$—CF$_3$, alkyl having 1, 2, 3, 4, 5 or 6 carbon atoms or cycloalkyl having 3, 4, 5, 6, 7 or 8 carbon atoms, wherein 1, 2, 3 or 4 hydrogen atoms may be substituted by fluorine atoms;

R11 and R12 are, independently of one another, hydrogen, alkyl having 1, 2, 3 or 4 carbon atoms or —CH$_2$—CF$_3$;

dd, ee and ff are, independently of one another, zero or 1;

gg is zero, 1 or 2;

hh is zero or 1;

jj is zero, 1, 2, 3 or 4;

kk is zero or 1;

or R4 is —(CH$_2$)$_{ll}$-phenyl or —O-phenyl, wherein the phenyl radicals are unsubstituted or substituted by 1, 2 or 3 radicals selected from the group consisting of F, Cl, Br, I, —O$_{mm}$—(CH$_2$)$_{nn}$—CF$_3$, alkoxy having 1, 2, 3 or 4 carbon atoms, alkyl having 1, 2, 3 or 4 carbon atoms, and —SO$_2$CH$_3$;

mm is zero or 1;

nn is zero, 1, 2 or 3;

ll is zero, 1, 2, 3 or 4;

or R4 is —(CH$_2$)$_{oo}$-heteroaryl, which is unsubstituted or substituted by 1, 2 or 3 radicals selected from the group consisting of F, Cl, Br, I, —O$_{pp}$—(CH$_2$)$_n$—CF$_3$, alkoxy having 1, 2, 3 or 4 carbon atoms, alkyl having 1, 2, 3 or 4 carbon atoms, and —SO$_2$CH$_3$;

pp is zero or 1;

rr is zero, 1, 2 or 3; and oo is zero, 1, 2, 3 or 4, said process comprising the step of:

reacting a compound of formula II,

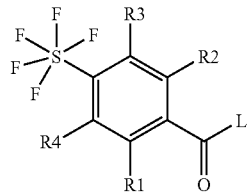

wherein R1 to R4 are as previously defined, and L is a leaving group which can undergo nucleophilic substitution, with guanidine.

7. The process of claim 6 wherein L is an alkoxy group, a phenoxy group, a phenylthio group, a methylthio group, a 2-pyridylthio group, a nitrogen heterocycle, a hydroxide, or a halogen.

8. The process of claim 7 wherein L is a methoxy, 1-imidazolyl, hydroxy, or Cl.

9. A medicament comprising the compound according to claim 1.

10. A medicament comprising the compound according to claim 3.

11. A medicament comprising the compound according to claim 4.

* * * * *